United States Patent [19]

Andersson et al.

[11] Patent Number: 5,055,459

[45] Date of Patent: Oct. 8, 1991

[54] SELECTIVE ELIMINATION OF MALIGNANT CELLS FROM BONE MARROW BY BIS (ACYLOXY) PROPYLPHOSPHORAMIDATES

[75] Inventors: Borje S. Andersson; David Farquhar, both of Houston, Tex.

[73] Assignee: Board of Regents, The University of Texas, Austin, Tex.

[21] Appl. No.: 335,016

[22] Filed: Apr. 6, 1989

Related U.S. Application Data

[63] Continuation-in-part of Ser. No. 879,910, Jun. 30, 1986, Pat. No. 4,841,085, and a continuation-in-part of Ser. No. 323,423, Mar. 14, 1989.

[51] Int. Cl.$^5$ .................... A01N 47/16; A01N 41/02; A01N 37/34
[52] U.S. Cl. .................................. 514/114; 514/118; 514/121; 514/129; 514/131
[58] Field of Search ............... 514/114, 118, 121, 129, 514/131

[56] References Cited

U.S. PATENT DOCUMENTS 4,841,085 6/1980 Farquhar et al. .................. 538/180

FOREIGN PATENT DOCUMENTS 0098601 6/1983 Fed. Rep. of Germany .
2429795 7/1977 France .

OTHER PUBLICATIONS

Filoslav Beran, Borje S. Andersson, Yugiang Wang, Kenneth B. McCredie, and David Farquhar: Cancer research 48, 339-345, Jan. 15, 1988. The Effects of Acetaldophosphamide, a Novel Stable Aldophosphamide Analogue, n Normal Human and Leukemic Progenitor Cells in Vitro: Implications for Use in Bone Marrow Purging.
A. Takamizawa et al.: Journal of the American Chemical Society, vol. 95, No. 3, 7 Feb. 1973. "Studies on cyclophosphamide metabolites and their related compounds. II. Preparation of an active species."
International Search Report for PCT/US 89/01214.

Sladek (1973), Cancer Res., 33:1150.
Conners, et al. (1974), Biochemical Pharmacol., 23:115.
Cox, et al. (1975), Cancer Res., 35:3755.
Friedman, et al. (1979), Adv. Cancer Chemother., 1:143.
Sharkis, et al. (1980), Blood, 55:521.
Korbling, et al. (1982), Brit. J. Haematol., 52:89.
Hilton, et al. (1984), Proc. Amer. Assoc. Cancer Res.
Hilton, (1984), Biochem. Pharmacol., 33:1867.
Hilton, (1984) Cancer Res., 44:5156.
Sladek, et al. (1985), Cancer Res., 45:1549.
Stewart, et al. (1985), Exp. Hematol, 13:267.
Struck, et al. (1975), Heyden and Son, Ltd.

(List continued on next page.)

Primary Examiner—Nathan M. Nutter
Attorney, Agent, or Firm—Arnold, White & Durkee

[57] ABSTRACT

A method for purging tumor cells from bone marrow of a host, the method comprising
extracting bone marrow cells from the host;
treating extracted bone marrow cells with a therapeutic level of a compound having the structure:

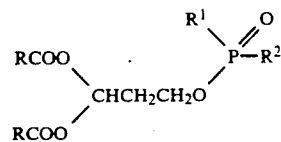

wherein R is $CH_3$, $C_2H_5$, $C_3H_7$, $t-C_4H_9$ or $C_6H_5$; $R^1$ is $NH_2$, $NHCH_3$, $NHC_2H_5$, $NHC_3H_7$, $NHC_4H_9$, $NHCH_2CH_2Cl$, $NHC_6H_5$, $N(CH_3)_2$, $N(C_2H_5)_2$, $N(C_3H_7)_2$, $NCH_3(C_2H_5)$, $NCH_3(C_3H_7)$, $N(CH_2CH_2Cl)_2$, $NHOH$, $NHNHCO_2CH_2C_6H_5$, $NHNHCO_2C(CH_3)_3$, $OCH_3$, $OC_2H_5$, $OC_3H_7$, $OC_4H_9$, $OC_6H_5$, $OCH_2C_6H_5$, $CH_3$, $C_2H_5$, $C_3H_7$, $C_4H_9$, $CH_2NO_2$ or $CH_2NH_2$; and $R^2$ is $NHCH_2CH_2Cl$ or $N(CH_2Ch_2Cl)_2$. Intravascularly infusion of the treated bone marrow cells into the host then serves to reimplant tumor-free marrow cells.

12 Claims, 14 Drawing Sheets

OTHER PUBLICATIONS

Norpoth, (1976), Cancer Treatment Reports, 60:437.
Peter, et al. (1976), Cancer Treatment Reports, 60:429.
Struck, (1976), Cancer Treatment Reports, 60:317.
Frei, et al. (1977), Cancer Treatment Reports, 61:1209.
Farquhar, et al. (1979), J. of Labelled Compounds and Radiopharmaceuticals, XVI:615.
Farquhar, et al. (1980), J. Labelled Compounds and Radiopharmaceuticals, XVII:159.
Zon, et al. (1982), J. Pharm. Sci., 71:443.
Farquhar, et al. (1983), J. Med. Chem., 26:1153.
Farquhar, et al. (1983), J. Pharmaceutical Sciences, 72:324.
Garattini, (1983), European J. of Drug Metabolism and Pharmacokinetics, 8:97.
Struck, et al., (1983), Brit. J. Cancer, 47:015-026.
Herve', (1984), Investigational New Drugs, 2:245.
Struck and Alberts, (1984), Cancer Treatment Reports, 68:765.
de Jong, et al., (1985), Cancer Res., 45:4001.
Gordon, et al. (1985), Leukemia Research, 9:1017.
Kohn and Sladek, (1985), Biochem. Pharmacol., 34:3465.
Smith and Sladek, (1985), Biochem. Pharmacol., 34:3459.
Yeager, et al., Jul. 17, 1986, The New England Journal of Medicine, vol. 315.
Kohn, (1987), Cancer Res. 47:3180.
Montgomery and Struck, (1976), Cancer Treatment Rep., 60:381.
Struck, (1974), Cancer Res., 34:2933.

COMPOUND 20-E : R = CH₃,
COMPOUND 21-E : R = CH₂CH₃

WITH DOXORUBICIN, X = OH

WITH DAUNOMYCIN, X = H

Fig. 7
Scheme 1

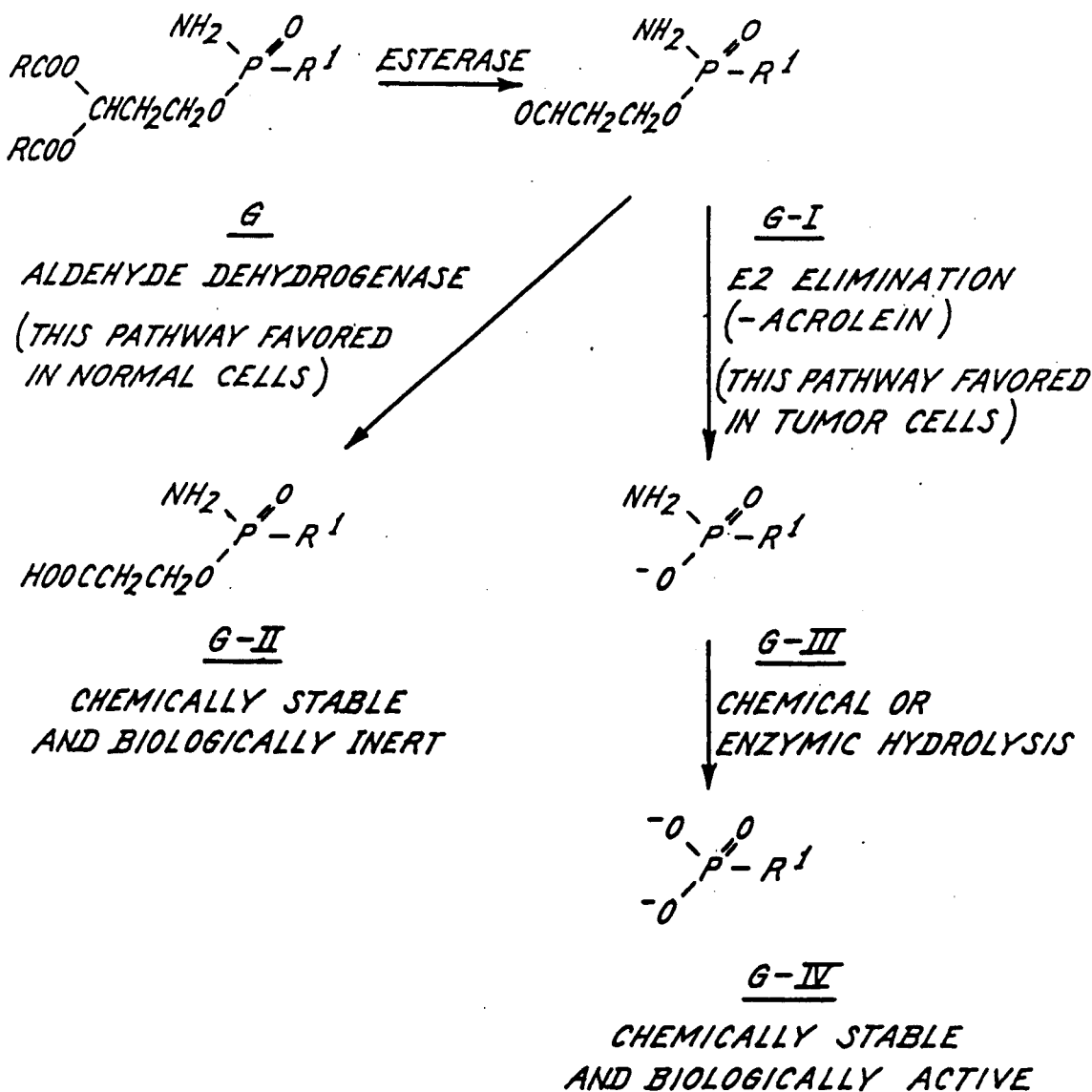

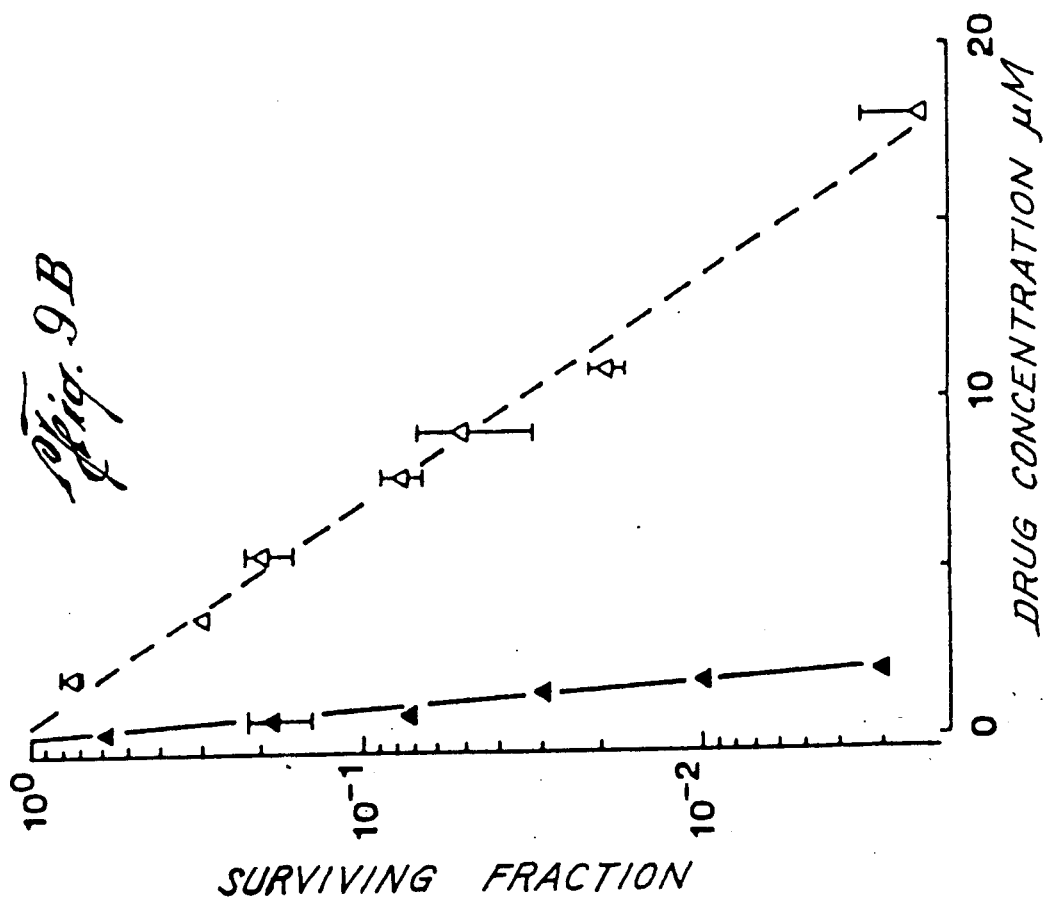
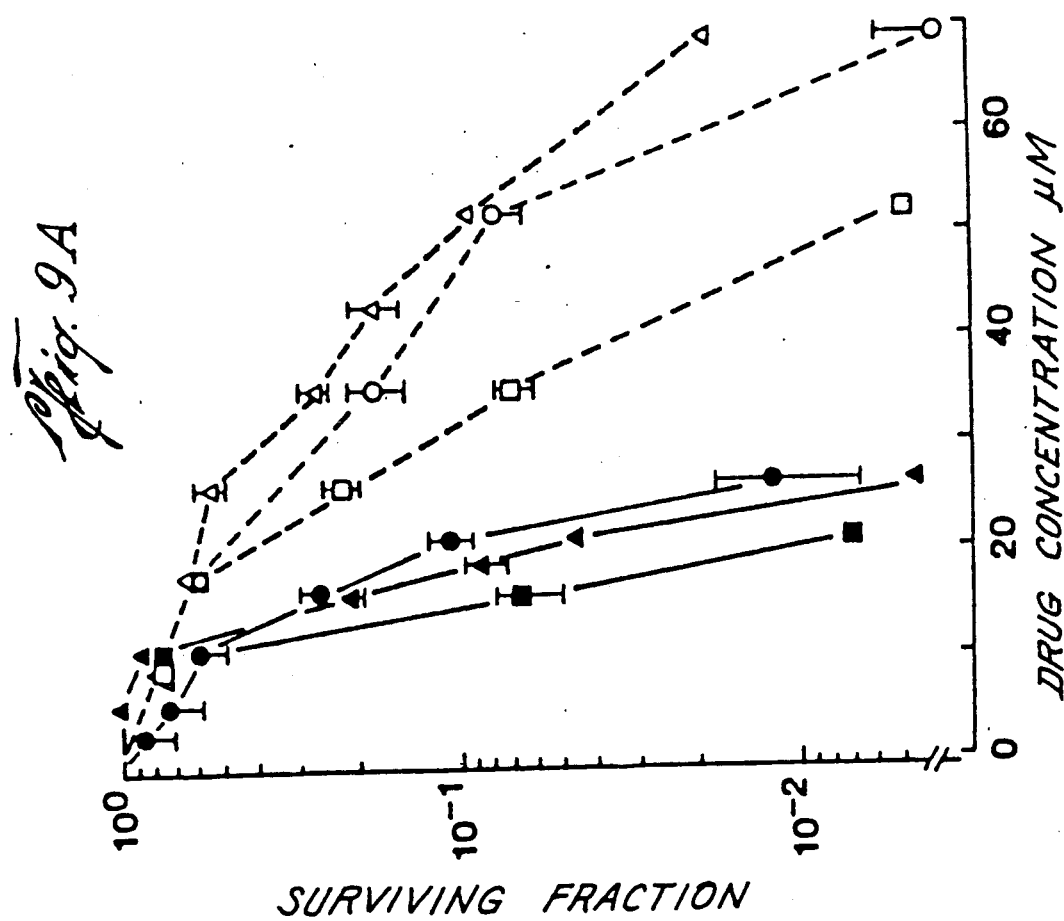
Fig. 9A
Fig. 9B

SELECTIVE ELIMINATION OF MALIGNANT CELLS FROM BONE MARROW BY BIS (ACYLOXY) PROPYLPHOSPHORAMIDATES

This is a continuation-in-part of Ser. No. 06/879,910 filed June 30, 1986; and Ser. No. 07/323,423 filed Mar. 14, 1989, now issued as U.S. Pat. No. 4,841,085, June 20, 1989.

BACKGROUND OF THE INVENTION

The present invention relates to cyclophosphamide analogs particularly useful for the suppression of tumor cells.

Since the demonstration in 1942 that nitrogen mustard was effective at inducing remissions in patients with lymphoma (A. Gilman Amer. J. Surg. 105:574), several thousand structural analogs have been synthesized in an attempt to enhance the selectivity of the parent drug. However, only a few of these compounds have demonstrated sufficient therapeutic superiority to nitrogen mustard in experimental tumor systems to warrant clinical trial. Of these, cyclophosphamide is unquestionably the most important. It has a higher therapeutic index than must other mustard-type alkylating agents and a much broader spectrum of clinical activity. However, the drug is not independently cytotoxic; it requires enzymatic activation in order to exert biologic activity. Although the biotransformation of cyclophosphamide, in vivo, is complex, the following general principles (FIG. 1) are widely accepted (D. L. Hill (1975) A Review of Cyclophosphamide (Charles C. Thomas, Springfield, Ill. and O. M. Friedman, et al. (1979) Adv. Cancer Chemother. 1:143).

As shown in FIG. 1, Cyclophosphamide, (1-A), is oxidatively biotransformed, mainly in the liver, by cytochrome P-450 dependent mixed-function oxidases to give 4-hydroxycyclophosphamide, (2-A). This metabolite exists in equilibrium with aldophosphamide (3-A), its open-chain tautomer. Aldophosphamide is labile and undergoes an E2 elimination reaction to generate phosphorodiamidic mustard (5-A) and acrolein (6-A). 4-Hydroxycyclophosphamide and aldophosamide also undergo further enzymatic oxidation, the former mediated by alcohol dehydrogenases and the latter by aldehyde dehydrogenases or aldehyde oxidases, to give, respectively, 4-ketocyclophosphamide (4-A) and carboxyphosphamide (7-A). Compounds 4-A and 7-A are chemically stable and relatively non-toxic. Phosphorodiamidic mustard (5), a potent alkylating agent, is generally considered to be the ultimate active metabolite of cyclophosphamide.

Although widespread agreement exists on the metabolism of cyclophosphamide, its mechanism of antitumor selectivity has been controversial. However, strong evidence has recently been presented in favor of the Selective Detoxification Hypothesis. The key feature of this hypothesis, first proposed by Sladek ((1973) Cancer Res. 33:1150), and later by Connors, et al. ((1974) Biochemical Pharmacol. 23:114), and Cox, et al. ((1975) Cancer Res. 35:3755), is that the conversion of aldophosphamide to carboxyphosphamide, a biologically inert compound, is less efficient in tumor cells than in most drug-susceptible normal cells (e.g., hematopoietic stem cells) because the latter contain higher levels of aldehyde dehydrogenases. As a consequence, more aldophosphamide dissociates to the highly cytotoxic demonstrated that intracellular levels of aldehyde dehydrogenases are, indeed, an important biologically-operative determinant of the antitumor selectivity of cyclophosphamide. Thus, Hilton and Colvin have shown (J. Hilton, et al. (1984) Proc. Amer. Assoc. Cancer Res. 5:339) that intracellular levels of aldehyde dehydrogenase correlate inversely with cyclophosphamide sensitivity both in a variety of human and rodent hematopoietic cell lines, and in human leukemic cells; high aldehyde dehydrogenase levels were present in drug-resistant cells. An L1210 resistant cell-line with unusually high aldehyde dehydrogenase activity was rendered drug-sensitive (J. Hilton (1984) Biochem. Pharmacol. 33:1867) by pretreating the cells with low concentrations of disulfiram, an aldehyde dehydrogenase inhibitor. Equally significant, 4-hydroxycyclophosphamide was extensively converted to carboxyphosphamide, an inactive metabolite, when incubated with extracts from the drug resistant L1210 cell-line (J. Hilton (1984) Cancer Res. 44:5156). By contrast, negligible levels of carboxyphosphamide, were formed when 4-hydroxycyclophosphamide was incubated, under the same conditions, with extracts from the drug-sensitive cell line. The author concluded (J. Hilton (1984) Cancer Res. 4:5156): '4-Hydroxycyclophosphamide and/or aldophosphamide is the form in which cyclophosphamide reaches these tumor cells in mice and that intracellular aldehyde dehydrogenase activity is an important determinant of cyclophosphamide sensitivity in these cell lines.

Sladek has reported (N. E. Sladek, et al. (1985) Cancer Res. 45:1549) that three known (and one suspected) inhibitors of aldehyde dehydrogenase activity [disulfiram, diethyl dithiocarbamate, cyanamide, and (ethylphenyl (2-formylethyl) phosphinate)] potentiate the cytotoxicity of 4-hydroperoxycyclophosphamide and ASTA Z 7557 (Conference proceedings published in: (1984) Investigational New Drugs 2:1–259), (both latent precursors of 4-hydroxycyclophosphamide) when incubated against cyclophosphamide-resistant L1210 and P-388 cell-lines. Significantly, no potentiation was observed with phosphordiamidic mustard, the presumed active metabolite of cyclophosphamide. In further studies, Sladek has shown (F. R. Kohn, et al. (1984) Proc. Amer. Assoc. Cancer Res. 25:289); (F. R. Kohn, et al. (In press) Biochem. Pharmacol) that aldehyde dehydrogenase activity is an important determinant of the differential sensitivities of murine pluripotent hematopoietic stem cells and granulocytemacrophage myeloid pregenitor cells to various activated cyclophosphamide analogs, including 4-hydroperoxycyclophosphamide and ASTA Z 7557. This finding likely accounts for the relative sparing effect of cyclophosphamide on myeloid stem cells.

Friedman, et al. (O. M. Friedman (1979) Adv. Cancer Chemother. 1:143) and, more recently, Zon (G. Zon (1982) Progress in Medicinal Chemistry 19:205) have strongly emphasized the need for further investigations in the mechanism of selectivity of cyclophosphamide and its analogs. The present application relates to new information that is critically relevant to this question. An important advantage of the present invention is the incorporation of structural and mechanistic features that contribute to the selectivity of cyclophosphamide into other antitumor drugs to enhance their therapeutic efficacy.

Advances in the treatment of acute myeloid leukemia in adults has generally been due to the introduction of new cytostatic drugs. The most important of these have been arabinosyl cytosine (Ara-C), the anthracyclines, and m-AMSA. Different combinations of these drugs give remission rates of about 60–70% (R. P. Gale (1977) Lancet 1:497); (J. F. Holland, et al. (1976) Arch. Intern. Med. 136:1377); and (K. B. McCredie, et al. (1981) Proc. A.S.C.O. and AACR 22:479); however, the median duration of complete remission is less than 18 months, with a "cured" fraction of less than 20%.

In contrast, long-term release-free survival can be achieved in about 50% of AML-patients after high-dose chemotherapy and total body irradiation followed by allogeneic bone marrow transplantation in first remission (R. A. Clift, et al. (1985) Blood 66(5):887 (Abstract); (A. Fefer, et al. (1983) Blood 57:421); and, (K. G. Blume, et al. (1980) N. Engl. J. Med. 302:1041). Similar results have been obtained in patients with relapsing or refractory acute leukemia who receive bone marrow transplantation from an identical twin, after supralethal chemoradiotherapy (R. L. Powles, et al. (1980) Lancet 1:1047). Unfortunately, only about 25% of all patients have an HLA-compatible sibling available or bone marrow donation. The patient,s own bone marrow can, however, be harvested in complete remission, cryopreserved, and used as a source of syngeneic hematopoietic stem cells for graftment purpose. This procedure allows a transplantation conditioning regimen with high-dose chemo-or chemoradiotherapy aimed at eradicating dormant leukemic cells in sanctuary sites like testicles, ovaries and the central nervous system. The problem that prevents more widespread use of cryopreserved autologous bone marrow is the presence of occult clonogeneic leukemic cells in remission bone marrow. Thus, results obtained with autologous bone marrow transplantation for AML in first remission do not differ significantly from that obtained with chemotherapy along (A. Fefer, et al. (1983) Blood 57:421). Ten evaluable patients were treated in second remission, with high-dose chemotherapy followed by autologous marrow transplant. Of those, one was alive in remission at 30 months, seven relapsed (range 1–8 months) and two died early. The feasibility of using in vitro immunologic or pharmacologic treatment of remission bone marrow to eliminate occult leukemic clonogeneic cells capable of causing relapse of the disease has been convincingly proven in animal model systems (P. Stewart, (1980) Blood 55:521); (H. Coizer, et al. (1982) Proc AACR 23:194); (M. Korbling, et al. (1982) Br. J. Haematol 52:89); and, (S. Thierfelder, et al. (1977) Eur J. Cancer 15:1357). Early data for in vitro treatment ("purging") of human remission bone marrow indicate that methodology can be designed that allows successful engraftment of the patients with in vitro manipulated marrow. The available methods that have been used so far include:

(a) treatment of bone marrow with antibodies plus complement;
(b) treatment with antibodies linked to a toxin e.g. ricin;
(c) pharmacologic treatment with an in vitro active drug.

The major weakness with the immunological "purging" methods is the lack of proven specific acute leukemia antigens that would distinguish leukemic cells from normal hemopoietic stem cells. Another technical problem is the limited availability of large quantities of monoclonal antibodies for in vitro treatment of large volumes of bone marrow.

For pharmacologic purging, the ideal drug(s) should preferably selectively kill leukemic stem cells while leaving the normal stem cells intact to allow for hemopoietic reconstitution. Obviously, such techniques alleviate the problem of finding specific anti-leukemia antibodies. Another advantage is that drug can easily be manufactured in large quantities under standardized conditions. One drug that has a possible selective action against leukemic versus normal cells is cyclophosphamide. Its in vitro active congener 4-hydroperoxycyclophosphamide, has recently received much attention for purging purposes both in murine models (P. Stewart, et al. (1985) Exp. Hematol. 13:267); (S. J. Sharkis, et al. (1980) Blood 55:521); (H. Coizer, et al. (1982) Proc AACR 23:194); (M. Korbling, et al. (1982) Br. J. Haematol. 52:89); (S. Thierfelder, et al. (1977) Eur. J. Cancer 15:1357); (E. S. Vitetta, et al. (1982) Immunol. Rev. 62:160) and in a clinical setting (A. Hagenbeck and A.C.M. Martens (1981) Exp. Hematol. 10 (Suppl. 11):14); (H. Kaizer, et al. (1981) Exp. Haematol. 9 (Suppl. 372):190) and, (L. Douay, et al. (1982) Exp. Hematol. 10 (Suppl. 12):113.

The major shortcomings of 4-hydroperoxycyclophosphamide (4-HC) is that it has a relatively short half-life in vitro (less than 2 hrs) and that its toxic action decreases with increasing cell concentration. Furthermore, the supply of doses is limited. To circumvent these shortcomings, a new series of in vitro active oxazaphosphorines is a subject of the present invention. The present application relates to investigating the in vitro activity of these compounds in human myeloid leukemic cell lines that have been developed and recently characterized, both the parent lines and sublines resistant to two of the other major anti-leukemic drugs, doxorubicin and m-AMSA in comparison to their action on normal committed myeloid stem cells and pluripotent hemopoietic stem cells. A long-term goal of the present invention enables the techniques that may be applied in clinical setting for autologous bone marrow transplantation.

Among the objectives of the present invention are:
(1) to develop a model for in vitro treatment of human bone marrow, obtained from patients with acute myeloid leukemia in complete remission, with a novel series of in vitro active oxazaphosphorines,
(2) to determine the optimal condition under which maximum leukemic clonogeneic cell kill can be achieved with sparing of hemopoietic regenerative capacity, (3) to examine possible quantitative differences between myeloid leukemic and normal hemopoietic stem cells in the make-up of activating and degrading enzymatic machinery responsible for the resulting cytotoxicity, and
(4) to explore different avenues of manipulating cellular aldehyde dehydrogenase activity, thereby augmenting differences in cytotoxicity between normal and leukemic clonogeneic stem cells.

SUMMARY OF THE INVENTION

The present invention involves a method for purging tumor cells, leukemic tumor cells, for example, from bone marrow of a host, the method comprising extracting bone marrow cells from the host;
treating extracted bone marrow cells with a therapeutic level of a compound having the structure:

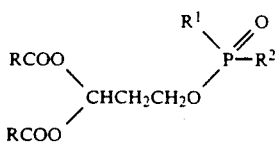

wherein R is CH$_3$, C$_2$H$_5$, C$_3$H$_7$, t-C$_4$H$_9$ or C$_6$H$_5$; R$^1$ is NH$_2$, NHCH$_3$, NHC$_2$H$_5$, NHC$_3$H$_7$, NHC$_4$H$_9$, NHCH$_2$CH$_2$Cl, NHC$_6$H$_5$, N(CH$_3$)$_2$, N(C$_2$H$_5$)$_2$, N(C$_3$H$_7$)$_2$, NCH$_3$(C$_2$H$_5$), NCH$_3$(C$_3$H$_7$), N(CH$_2$CH$_2$Cl)$_2$, NHOH, NHNHCO$_2$CH$_2$C$_6$H$_5$, NHNHCO$_2$C(CH$_3$)$_3$, OCH$_3$, OC$_2$H$_5$, OC$_3$H$_7$, OC$_4$H$_9$, OC$_6$H$_5$, OCH$_3$C$_6$H$_5$, CH$_3$, C$_2$H$_5$, C$_3$H$_7$, C$_4$H$_9$, CH$_2$NO$_2$ or CH$_2$NH$_2$; and R$^2$ is NHCH$_2$CH$_2$Cl or N(CH$_2$CH$_2$Cl)$_2$. Intravascular infusion of the treated bone marrow cells into the host then serves to reimplant tumor-free marrow cells.

In one view, the present invention involves bone marrow purging using a compound having the structure:

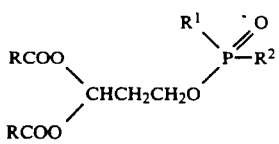

wherein R is CH$_3$, C$_2$J$_5$, C$_3$H$_7$, t-C$_4$H$_9$ or C$_6$H$_5$; R$^1$ is NH$_2$, NHCH$_3$, NHC$_2$H$_5$, NHC$_3$H$_7$, NHC$_4$H$_9$, NHCH$_2$CH$_2$Cl, NHC$_6$H$_5$, N(CH$_3$)$_2$, N(C$_2$H$_5$)$_2$, N(C$_3$H$_7$)$_2$, NCH$_3$(C$_2$H$_5$), NCH$_3$(C$_3$H$_7$), N(CH$_2$CH$_2$Cl)$_2$, NHOH, NHNHCO$_2$CH$_2$C$_6$H$_5$, NHNHCO$_2$C(CH$_3$)$_3$, OCH$_3$, OC$_2$H$_5$, OC$_3$H$_7$, OC$_4$H$_9$, OC$_6$H$_5$, OCH$_2$C$_6$H$_5$, CH$_3$, C$_2$H$_5$, C$_3$H$_7$, C$_4$H$_9$, CH$_2$NO$_2$ or CH$_2$N$_2$ and R$^2$ is NHCH$_2$CH$_2$Cl or N(CH$_2$CH$_2$Cl)$_2$.

Any one of these compounds may be used to eliminate occult tumor cells such as leukemic clonogenic cells from bone marrow by contacting the bone marrow with a solution comprising sufficient levels of said compound. Analogously, tumor cells in a host or organ of a host may be eliminated by treatment of the host or host's organ with a compound of this description.

Compounds of this description are also usable in the purging method of the present in;ention may be stable aldophosphamide analogs activatable by the action of an esterase and a subsequent elimination reaction to form acrolein and a phosphoramidic mustard of the formula:

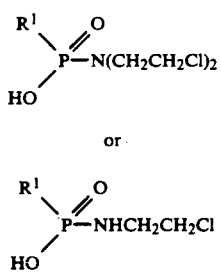

wherein R$^1$ is NH$_2$, NHCH$_3$, NHC$_2$H$_5$, NCH$_3$H$_7$, NHC$_4$H$_9$, NHCH$_2$CH$_2$Cl, NHC$_6$H$_5$, N(CH$_3$)$_2$, N(C$_2$H$_5$)$_2$, N(C$_3$H$_7$)$_2$, NCH$_3$(C$_2$H$_5$), NCH$_3$(C$_3$H$_7$), N(CH$_2$CH$_2$Cl)$_2$, NHOH, NHNHCO$_2$CH$_2$C$_6$H$_5$, NHNHCO$_2$C(CH$_3$)$_3$, OCH$_3$, OC$_2$H$_5$, OC$_3$H$_7$, OC$_4$H$_9$, OC$_6$H$_5$, OCH$_2$C$_6$H$_5$, CH$_3$, C$_2$H$_5$, C$_3$H$_7$, C$_4$H$_9$, CH$_2$NO$_2$ or CH$_2$NH$_2$.

The methods of the present invention may be further described as involving usage of a compound having the structure

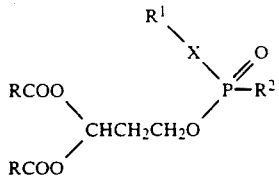

wherein:

R is alkyl, aryl, or alkaryl;

X is N, NH, NHNH, NHO, ONH, alkyl;

R$^1$ is hydrogen, alkyl, dialkyl, aryl, chloroalkyl, nitro, amine, benzyloxycarbonyl or t-butoxycarbonyl; and R$^2$ is chloroethylamine or bis(chloroethyl)amine.

Additionally usable in the methods of the present invention is a compound having the structure:

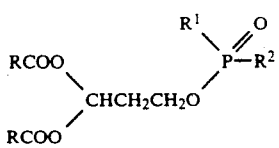

wherein:

R is CH$_3$, C$_2$H$_5$, C$_3$H$_7$, t-C$_4$H$_9$ or C$_6$H$_5$;

R$^1$ is NH$_2$, NHCH$_3$, NHC$_2$H$_5$, NHC$_3$H$_7$, NHC$_4$H$_9$, NHCH$_2$CH$_2$Cl, NHC$_6$H$_5$, N(CH$_3$)$_2$, N(C$_2$H$_5$)$_2$, N(C$_3$H$_7$)$_2$, NCH$_3$(C$_2$H$_5$), NCH$_3$(C$_3$H$_7$), N(CH$_2$CH$_2$Cl)$_2$, NHOH, NHNHCO$_2$CH$_2$C$_6$H$_5$, NHNHCO$_2$C(CH$_3$)$_3$, OCH$_3$, OC$_2$H$_5$, OC$_3$H$_7$, OC$_4$H$_9$, OC$_6$H$_5$, OCH$_2$C$_6$H$_5$, CH$_3$, C$_2$H$_5$, C$_3$H$_7$, C$_4$H$_9$, CH$_2$NO$_2$ or CH$_2$NH$_2$; and R$^2$ is NHCH$_2$CH$_2$Cl or N(CH$_2$CH$_2$Cl)$_2$.

In broader view, the present invention describes methods involving stable aldophosphamide analogs activatable by the action of an esterase and a subsequent spontaneous E-2 elimination reaction to form acrolein and a phosphoramidic mustard, said phosphoramidic mustard having the formula

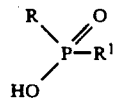

wherein:

R is NH$_2$, NHCH$_3$, NHC$_2$H$_5$, NHC$_3$H$_7$, NHC$_4$H$_9$, NHCH$_2$CH$_2$Cl, NHC$_6$H$_5$, N(CH$_3$)$_2$, N(C$_2$H$_5$)$_2$, N(C$_3$H$_7$)$_2$, NCH$_3$(C$_2$H$_5$), NCH$_3$(C$_3$H$_7$), N(CH$_2$CH$_2$Cl)$_2$, NHOH, NHNHCO$_2$CH$_2$C$_6$H$_5$, NHNHCO$_2$C(CH$_3$)$_3$, OCH$_3$, OC$_2$H$_5$, OC$_3$H$_7$, OC$_4$H$_9$, OC$_6$H$_5$, OCH$_2$C$_6$H$_5$, CH$_3$, C$_2$H$_5$, C$_3$H$_7$, C$_4$H$_9$, CH$_2$NO$_2$ or CH$_2$NH$_2$; and R$^1$ is NHCH$_2$CH$_2$Cl or N(CH$_2$CH$_2$Cl)$_2$.

Additionally, the method of the present invention involves a compound having the structure:

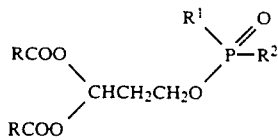

wherein:
R is $CH_3$, $C_2H_5$, $C_3H_7$, $C(CH_3)_2$ or $C_6H_5$;
$R^1$ is $NH_2$, $NHCH_3$, $NHCH_2CH_3$, $NHCH_2CH_2Cl$, $N(CH_3)_2$, $N(CH_2CH_3)_2$, $N(CH_2CH_2Cl)_2$, $NHCH_2CH_2CH_2CH_3$, $NCH_3(C_2H_5)$, $NCH_3(C_3H_7)$, $NHC_6H_5$, $NHOH$, $NHNHCO_2CH_2C_6H_5$, $NHNHCO_2C(CH_3)_3$, $OCH_3$, $OCH_2CH_3$, $OC_3H_7$, $OC_4H_9$, $OC_6H_5$, $OCH_2C_6H_5$, $ONHCO_2C(CH_3)_3$, $OCH_2CH_2CH(OAc)_2$, $OP(O)N(CH_2CH_2Cl)_2$, $CH_3$, $CH_2CH_3$, $CH_2CH_2CH_3$, $CH_2CH_2CH_2CH_3CH_2NO_2$, or $CH_2NH_2$; and
$R^2$ is $N(CH_2CH_2Cl)_2$ or $NHCH_2CH_2Cl$.

Compounds of the present inventive method include those having the structure:

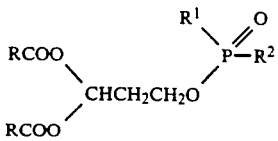

wherein:
R is $CH_3$, $C_2H_5$, $C_3H_7$, $C(CH_3)_3$ or $C_6H_5$;
$R^1$ is a cytotoxic glycoside; and
$R^2$ is $N(CH_2CH_2Cl)_2$ or $NHCH_2CH_2Cl$.

In more particularity, the $R^1$ cytotoxic glycoside is N-(3')-doxorubicin or N-(3')-daunorubicin. Such derivatives should be selectively activated in tumor cells and be effective chemotherapeutic agents.

Another chemotherapeutic compound utilizable in the method of the present invention is one having the structure:

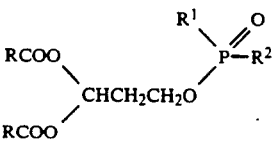

wherein:
R is $CH_3$, $C_2H_5$, $C_3H_7$, $C(CH_3)_2$ or $C_6H_5$;
$R^1$ is $NH_2$; and
$R^{b2}$ is a nucleoside.

Preferred $R^2$ nucleosides are 2',3'-dideoxyuridine-5'-yl and 5-methyl-2',3'- dideoxyuridin-5'-yL

BRIEF DESCRIPTION OF THE DRAWINGS

FIG. 7 shows the proposed activation mechanism of compounds of the present invention.

FIG. 8 shows the anticipated mechanism of action of compounds of the present invention.

FIG. 9A shows, the comparative cytotoxicity of acetaldoifosphamide (solid symbols) and 4-HC (open symbols) to mononuclear cells from normal bone marrow of three different human donors. The cells from each marrow were exposed to the two drugs in parallel at $2 \times 10^6$ cells for 60 min at 37° C. Each point is the mean +S.D. of triplicate cultures. The range of $IC_{50}$ values for acetaldoifosphamide was 11.5-12.5 uM, and the range of $IC_{50}$ values for 4-HC was 19-26 uM.

FIG. 9B shows comparative cytoxicity of acetaldoifosphamide (solid triangles) and 4-HC (open triangles) to the human myeloid cell line KBM-3. Each point is the mean ±S.D. of triplicate cultures from three separate experiments.

DESCRIPTION OF THE PREFERRED EMBODIMENTS

Figure 1:
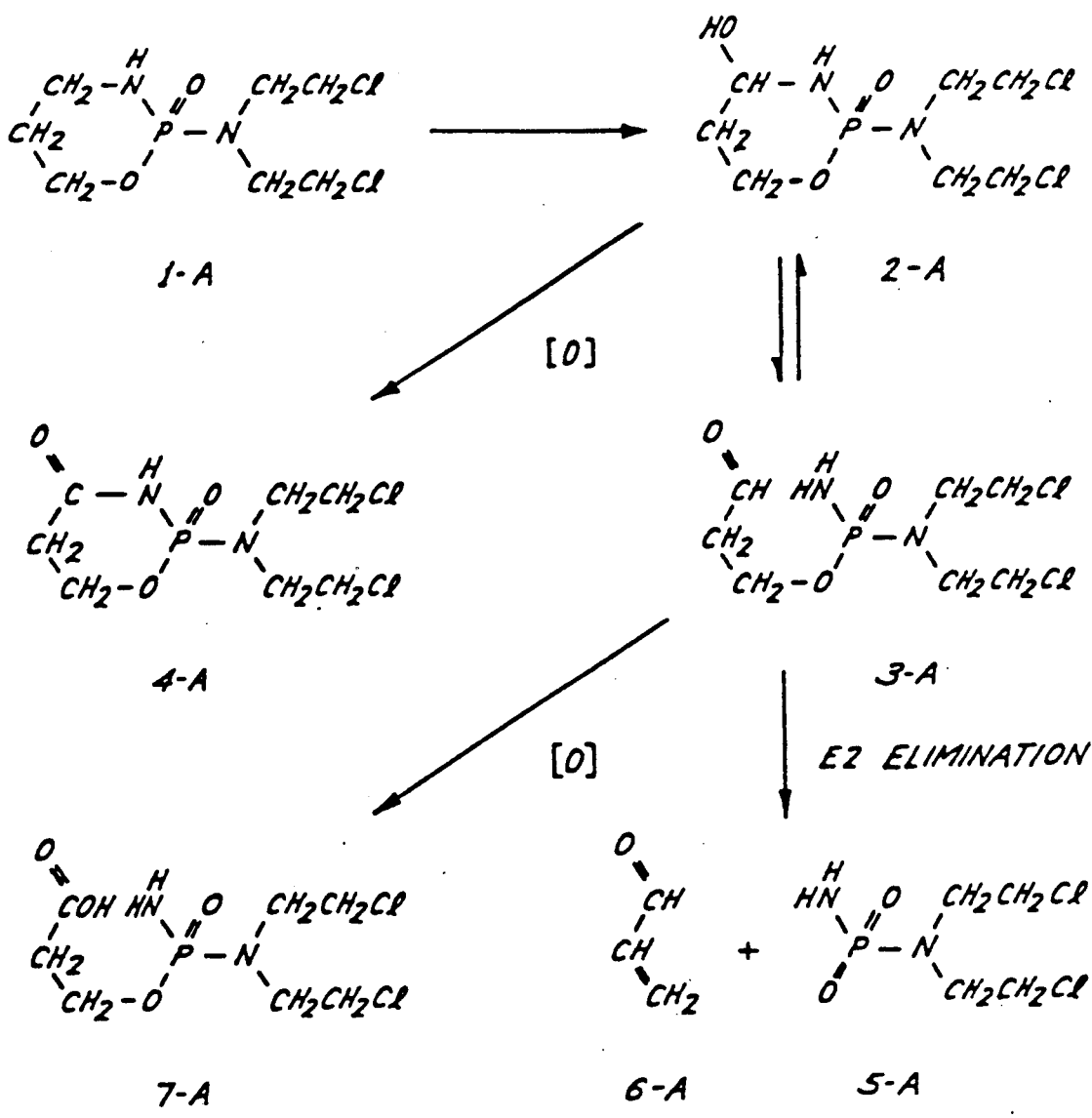
FIG. 1 schematically shows the generally accepted pathway for cyclophosphamide metabolism.

Objectives of this invention include the synthesis, biological evaluation and therapeutic use of a series of analogs of aldophosphamide, one of the major primary metabolites of cyclophosphamide. The analogs are designed to elucidate the structural correlates of antitumor activity for this general class of compounds, particularly the contribution of intermediate '4-hydroxy' cyclic structures to drug selectivity. A further major goal is to extend these key structural features to other cytotoxic agents in an attempt to enhance their therapeutic efficacy.

Novel aspects of studies with aldophosphamide analogs have shown that the analogs, unlike aldophosphamide, are chemically stable under neutral aqueous conditions. However, in the presence of carboxylate hydrolases (esterases), they will convert rapidly to unstable intermediates. Some of these intermediates can form cyclic derivatives, and exhibit chemical and biologic properties similar to those of aldophosphamide; other analogs which cannot cyclize, may exhibit substantially different properties. Correlation of the biologic properties of these compounds with their physicochemical characteristics should help clarify the structural correlates of antitumor selectivity.

Many compounds of the present invention are comprised in the following list. These new compounds have the following general structure:

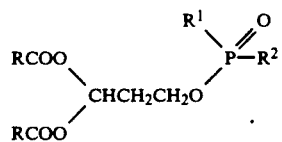
B

Where R, $R^1$ and $R^2$ are shown in Table 1 below for fifty-three model compounds.

TABLE 1

| Compound No. | R | $R^1$ | $R^2$ |
|---|---|---|---|
| B-1) | $CH_3$ | $NH_2$ | $N(CH_2CH_2Cl)_2$ |
| B-2) | $CH_3$ | $NHCH_3$ | $N(CH_2CH_2Cl)_2$ |
| B-3) | $CH_3$ | $NHCH_2CH_3$ | $N(CH_2CH_2Cl)_2$ |
| B-4) | $CH_3$ | $NHCH_2CH_2Cl$ | $N(CH_2CH_2Cl)_2$ |
| B-5) | $CH_3$ | $N(CH_3)_2$ | $N(CH_2CH_2Cl)_2$ |
| B-6) | $CH_3$ | $N(CH_2CH_3)_2$ | $N(CH_2CH_2Cl)_2$ |
| B-7) | $CH_3$ | $N(CH_2CH_2Cl)_2$ | $N(CH_2CH_2Cl)_2$ |
| B-8) | $CH_3$ | $OCH_3$ | $N(CH_2CH_2Cl)_2$ |
| B-9) | $CH_3$ | $OCH_2CH_3$ | $N(CH_2CH_2Cl)_2$ |
| B-10) | $CH_3$ | $CH_3$ | $N(CH_2CH_2Cl)_2$ |
| B-11) | $CH_3$ | $CH_2CH_3$ | $N(CH_2CH_2Cl)_2$ |
| B-12) | $CH_3$ | $NHCH_2CH_2Cl$ | $NHCH_2CH_2Cl$ |
| B-13) | $C_2H_5$ | $NH_2$ | $N(CH_2CH_2Cl)_2$ |
| B-14) | $C_2H_5$ | $NHCH_3$ | $N(CH_2CH_2Cl)_2$ |
| B-15) | $C_2H_5$ | $NHCH_2CH_2Cl$ | $NHCH_2CH_2Cl$ |
| B-16) | $C_2H_5$ | $NHCH_2CH_2Cl$ | $N(CH_2CH_2Cl)_2$ |
| B-17) | $C_2H_5$ | $N(CH_2CH_2Cl)_2$ | $N(CH_2CH_2Cl)_2$ |
| B-18 | $CH_3$ | $NHCH_2CH_2CH_3$ | $N(CH_2CH_2Cl)_2$ |
| B-19 | $CH_3$ | $NHCH_2CH_2CH_2CH_3$ | $N(CH_2CH_2Cl)_2$ |
| B-20 | $CH_3$ | $NCH_3(C_2H_5)$ | $N(CH_2CH_2Cl)_2$ |
| B-21 | $CH_3$ | $NCH_3(C_3H_7)$ | $N(CH_2CH_2Cl)_2$ |
| B-22 | $CH_3$ | $NHC_6H_5$ | $N(CH_2CH_2Cl)_2$ |
| B-23 | $CH_3$ | $NHOH$ | $N(CH_2CH_2Cl)_2$ |
| B-24 | $CH_3$ | $NHNHCO_2CH_2C_6H_5$ | $N(CH_2CH_2Cl)_2$ |
| B-25 | $CH_3$ | $NHNHCO_2C(CH_3)_3$ | $N(CH_2CH_2Cl)_2$ |
| B-26 | $CH_3$ | $OC_3H_7$ | $N(CH_2CH_2Cl)_2$ |
| B-27 | $CH_3$ | $OC_4H_9$ | $N(CH_2CH_2Cl)_2$ |
| B-28 | $CH_3$ | $OC_6H_5$ | $N(CH_2CH_2Cl)_2$ |

TABLE 1-continued

| Compound No. | R | $R^1$ | $R^2$ |
|---|---|---|---|
| B-29 | $CH_3$ | $OCH_2C_6H_5$ | $N(CH_2CH_2Cl)_2$ |
| B-30 | $CH_3$ | $ONHCO_2C(CH_3)_3$ | $N(CH_2CH_2Cl)_2$ |
| B-31 | $CH_3$ | $OCH_2CH_2CH(OAc)_2$ | $N(CH_2CH_2Cl)_2$ |
| B-32 | $CH_3$ | $OP(O)N(CH_2CH_2Cl)_2$ | $N(CH_2CH_2Cl)_2$ |
| B-33 | $CH_3$ | $CH_2CH_2CH_3$ | $N(CH_2CH_2Cl)_2$ |
| B-34 | $CH_3$ | $CH_2CH_2CH_2CH_3$ | $N(CH_2CH_2Cl)_2$ |
| B-35 | $CH_3$ | $CH_2NO_2$ | $N(CH_2CH_2Cl)_2$ |
| B-36 | $CH_3$ | $CH_2NH_2$ | $N(CH_2CH_2Cl)_2$ |
| B-37 | $CH_3$ | $CH_2CH_2CH_3$ | $N(CH_2CH_2Cl)_2$ |
| B-38 | $CH_3$ | $CH_2CH_2CH_2CH_3$ | $N(CH_2CH_2Cl)_2$ |
| B-39 | $C_3H_7$ | $NH_2$ | $N(CH_2CH_2Cl)_2$ |
| B-40 | $C_3H_7$ | $NHCH_3$ | $N(CH_2CH_2Cl)_2$ |
| B-41 | $C_3H_7$ | $NHCH_2CH_2Cl$ | $NHCH_2CH_2Cl$ |
| B-42 | $C_3H_7$ | $NHCH_2CH_2Cl$ | $N(CH_2CH_2Cl)_2$ |
| B-43 | $C_3H_7$ | $N(CH_2CH_2Cl)_2$ | $N(CH_2CH_2Cl)_2$ |
| B-44 | $C(CH_3)_3$ | $NH_2$ | $N(CH_2CH_2Cl)_2$ |
| B-45 | $C(CH_3)_3$ | $NHCH_3$ | $N(CH_2CH_2Cl)_2$ |
| B-46 | $C(CH_3)_3$ | $NHCH_2CH_2Cl$ | $NHCH_2CH_2Cl$ |
| B-47 | $C(CH_3)_3$ | $NHCH_2CH_2Cl$ | $N(CH_2CH_2Cl)_2$ |
| B-48 | $C(CH_3)_3$ | $N(CH_2CH_2Cl)_2$ | $N(CH_2CH_2Cl)_2$ |
| B-49 | $C_6H_5$ | $NH_2$ | $N(CH_2CH_2Cl)_2$ |
| B-50 | $C_6H_5$ | $NHCH_3$ | $N(CH_2CH_2Cl)_2$ |
| B-51 | $C_6H_5$ | $NHCH_2CH_2Cl$ | $NHCH_2CH_2Cl$ |
| B-52 | $C_6H_5$ | $NHCH_2CH_2Cl$ | $N(CH_2CH_2Cl)_2$ |
| B-53 | $C_6H_5$ | $N(CH_2CH_2Cl)_2$ | $N(CH_2CH_2Cl)_2$ |

The mechanism of activation of these compounds can be illustrated with respect to compound B-1. In the presence of carboxylate esterase, one of the carboxylate ester bonds of compound B-1(1-C in FIG. 2) is cleaved (FIG. 2) to generate the corresponding hemiacetal, 2-C. This compound then undergoes cleavage of the second ester group to give the hydrate, 3-C, which exists in equilibrium with the free aldehyde, 4-C. The hemiacetal, 2-C, may also spontaneously eliminate acetic acid to give the aldehyde, 4-C, directly. Once generated, the aldehyde, 4-C, will rapidly tautomerize to form an equilibrium mixture with 4-hydroxycyclophosphamide, 5-C. However, since aldehyde, 4-C, is inherently chemically labile, the tautomeric mixture will gradually dissociate by an E2 elimination reaction to generate the potently cytotoxic phosphoramide mustard, 6-C, and acrolein, 7-C.

The biologic properties of the new latent aldophosphamides are dependent on the steric and electronic character of the R, $R^1$, and $R^2$ substituents, since these parameters influence (1) the rate at which the compounds are bioactivated (2) the position of equilibrium of the aldophosphamide/4-hydroxycyclophosphamide tautomeric mixtures (3) the susceptibilities of the aldophosphamides to E2 elimination and (4) the chemical reactivities of the ultimate alkylating phosphoramide mustards. An understanding of the contribution of these substituents to the antitumor and immunosuppressive properties of this novel class of compounds is vital to the application of the above concepts in the design of further new organophosphate therapeutic agents.

These new compounds have many potential applications in medicine, particularly clinical oncology. One important application, autologous bone marrow transplantation, has already been mentioned. Another is the regional perfusion of tumors. Yet another is the local treatment of organ (e.g., pleural) tumor effusions. The new agents are also well suited to in vitro tumor sensitivity determination prior to systemic drug administration. However, long range goals relating to the present invention are to exploit the above concepts to develop new structural types of antitumor and immunosuppressive agents that exert their activities by molecular mechanisms fundamentally different from that of cyclophosphamide. The potential to develop such agents is now at hand.

The present invention comprises synthesis and uses of stable precursors of aldophosphamide that convert rapidly to the free aldehyde under physiologic conditions. Despite extensive endeavor, this has never been accomplished before. An excellent review of this entire area of investigation has been provided by Zon et al. (G. Zon (1982) Progress in Medicinal Chemistry 19:205). Currently, all preactivated analogs of cyclophosphamide that are used as experimental tools or that possess clinical promise (e.g. 4-hydroxycyclophosphamide, 4-hydroperoxycyclophosphamide, ASTA Z 7557), are cyclic structures that give rise to the ultimate active metabolites through the intermediacy of 4-hydroxycyclophosphamide. Major stability and formulation problems exist with many of these compounds. The opportunity to conduct mechanistic and therapeutic studies on analogs that initially give rise to aldophosphamide or to closely related structures, some of which cannot cyclize, has never before existed. Stable, open-chain aldophosphamide precursors that facilely generate the corresponding free aldehydes under physiologic conditions are inherently chemically and biologically interesting. Clearly, they are as useful, both as experimental tools and as clinical agents, as the ASTA series of compounds prepared in Germany that are the focus of intense experimental and clinical investigation and was the subject of a major international conference (Conference proceedings published (1984) Investigational New Drugs 2:1-259).

An unlimited number of stable, chemically-diverse, aldophosphamide analogs can readily be prepared using the approach described herein. Since the activating esterases are ubiquitous in tissue (K. Krisch (1971) The Enzymes 5:44, Academic Press), the compounds will facilely convert to the corresponding free aldehydes in all biological media, including tissue culture. The approach, therefore, is extremely broad in scope. By contrast, only a few 'preactivated' cyclic analogs are known. These latter compounds are synthesized from cyclophosphamide by a stepwise sequence in low overall yield. They are difficult to purify and are inherently chemically labile. Moreover, their limited availability and high cost are prohibitive of their widespread clinical use. It is not surprising that few such compounds have been reported, and that systemic structure/activity relationship studies with three compounds have never been undertaken. In addition cellular pharmacology studies with cyclic preactivated analogs are exceedingly difficult because radiolabeled formulations are not readily accessible. By comparison, none of these problems exist with the aldophosphamide analogs of the present invention.

The requirement for cyclic structural geometry places severe constraints on the types of analogs that can be prepared, severely limiting structure activity studies. These considerations are far from academic because the mechanistic principles that contribute to the antitumor selectivity of cyclophosphamide should be extendable, in principle, to a wide variety of other structures but be unrealizable, in practice, because of the severe molecular constraints imposed by the ring configuration. Using the new approach of the present invention, virtually any conceivable analog of the general formulae, C, described below, can now be readily prepared (for structure-activity relationship studies, if necessary) with the important added assurance that it will almost certainly be activated in vivo. This approach cannot even be considered using cyclic structures.

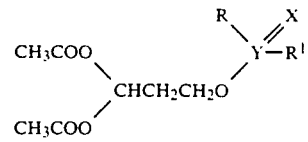

Wherein Y is P or S; X is O, S or NZ (Z is H or alkyl); one or both of R and $R^1$ is (are) cytotoxins (when only one is a cytotoxin, the other is H, $CH_2Z$, $NZ_2$,) OZ or SZ (where Z is H or alkyl)). Typical cytotoxins include doxorubicin, nucleoside derivatives and phosphoramidic mustards.

One major application of the strategy, and one that constitutes an important object of the invention described herein, is to extend the above principles to antitumor nucleosides in order to enhance their therapeutic efficacy.

A series of cyclophosphamide analogs has been synthesized and evaluated to elucidate their mechanism of oncostatic selectivity for cancer cells. The $ED_{50}$ values of these compounds against L1210 lymphatic leukemia cells have been determined. Some of these analogs have been found to have a greater therapeutic efficancy than ASTA Z 7557 with an in vitro assay.

Cyclophosphamide(1-A) shown in FIG. 1, is a widely used antitumor drug. Its metabolism has been well known (FIG. 1). It is first activated in liver by "mixed-function" oxidases to give the intermediate 4-hydroxycyclophosphamide(2-A), which undergoes a rapidly equilibrium with its open-chain tautomer aldophosphamide(3-A). The aldophosphamide degrades spontaneously to give 3-carbon-unit acrolein(4-A) and the ultimate cytotoxic moiety, phosphoramide mustard(5-A). During the biotransformation process. Some other reactions also occur. 4-Hydroxycyclophosphamide is reduced by dehydrogenases to give 4-ketocyclophosphamide(6-A), which is biologically inactive. Aldophosphamide is reduced by either aldehyde dehydrogenases or aldehyde oxidases or both to give carboxyphosphamide(7-A), which is non-toxic.

Although this pathway of cyclophosphamide metabolism has been generally accepted, less is known with certainty about the mechanisms of the cytotoxic selectivity of the cyclophosphamide. It has been proposed, as mentioned earlier herein, that the conversion of aldophosphamide to carboxyphosphamide, a biologically inactive metabolite, is less efficient in tumor cells than in normal cells because the tumor cells contain less aldehyde dehydrogenases than the normal cells. As a consequence, more of the highly cytotoxic phosphoramide mustard, which is considered to be the 'ultimate active metabolite', is formed from the aldophosphamide in the tumor cells.

The present invention concerns a series of compounds which are chemically stable, but are converted to aldehyde compounds rapidly in the presence of carboxylate esterases. Some of these compounds can cyclize but some cannot.

Certain compounds of the present invention may be expressed as having the structure

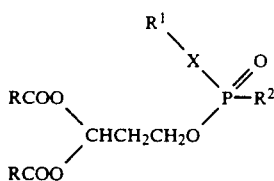

wherein R is alkyl, aryl, or alkaryl; X is N, NH, NHNH, NHO, ONH, or alkyl; $R^1$ is hydrogen, alkyl, dialkyl, aryl, chloroalkyl, nitro, amino, benzyloxycarbonyl or t-butoxycarbonyl; $R^2$ is chloroethylamine or bis(chloroethyl)amine.

Occult leukemic clonogenic cells may be eliminated from bone marrow by contacting the bone marrow with a solution comprising a sufficient level of one or more of the above compounds. Tumor cells from a host or an organ of a host may be likewise eliminated. A sufficient level of one or more of the above compounds is generally between about 5 mg/ml and about 30 mg/ml.

The compounds of the present invention represent new and effective tools for selectively eliminating occult leukemic clonogenic cells from bone marrow.

The following examples are presented to describe preferred embodiments and utilities of the present invention and are not meant to limit the present invention unless otherwise stated in the claims appended hereto.

EXAMPLE 1

Synthesis of Aldophosphamide Analogs

Figure 3:
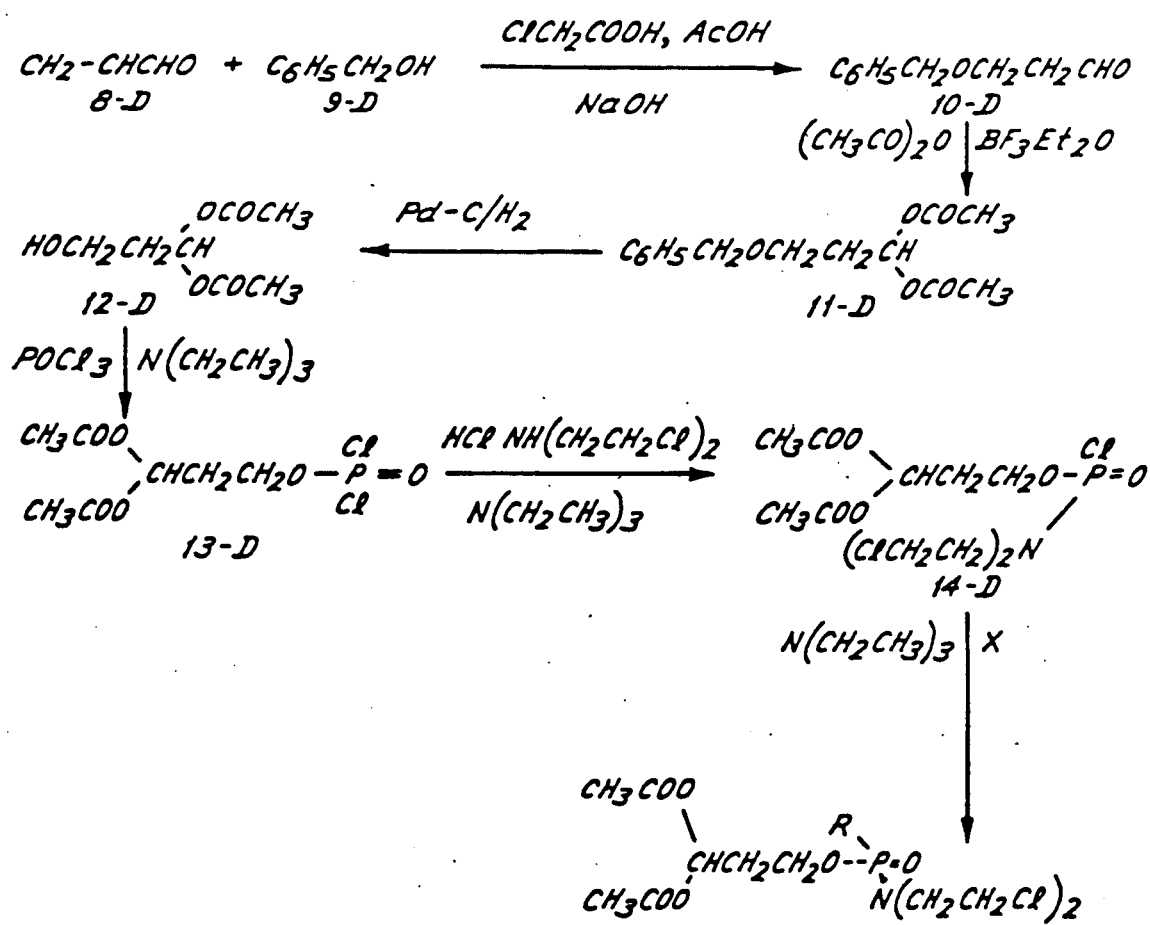
FIG. 3 schematically shows a synthetic pathway for compounds of the present invention.

The synthetic pathways are shown in FIG. 3. Acrolein, 8-D, was reacted with benzyl alcohol, 9-D, in the presence of monochloroacetic acid, acetic acid and sodium hydroxide as a catalyst, to give compound 10-D (Yamaguchi, et al. (1971) Chem. Abs. 74:523). Compound 10-D and acetic anhydride reacted rapidly to give compound 11-D in the presence of boron trifluoride/diethyl etherate (Edmund L. Niedzielski (1966) Chem. Abs. 65:6980). Compound 11-D was hydrogenolized over palladium-oncharcoal to give compound 12-D, which was crystallized with cooling. 1 equivalent of compound 12-D and triethylamine were added to 3 equivalents of phosphorus oxychloride (Takamizawa, et al., J. Med. Chem. 18 4.376) then 1 equivalent of bis(2-chloroethyl)amine hydrochloride and triethylamine were added. When the reaction was completed, the reaction mixture was washed with water and phosphate buffer, subjected to column chromatography, and eluted with ethylacetate and hexane. Compound 14-D was obtained as an oil. The amine [$NH_3$, HCl $NH_2CH_3$, HCl $NH_2CH_2CH_3$, HCl $N(CH_3)_2$, or $NH(CH_2CH_3)_2$] was reacted with 14-D to give compound 15-D, 16-D, 17-D, 18-D or 19-D respectively (FIG. 3).

The acrolein (99%), benzyl alcohol (99%), acetic anhydride (A.C.S. reagent), phosphorous oxychloride (99%), bis(2-chloroethyl)amine hydrochloride (98%), ethylamine (anhydrous, 99%), dimethylamine hydrochloride (97%), diethyl amine (98%), methanol (99.9+%), ethanol (anhydrous), and 2-chloroethylamine hydrochloride (98%), were all purchased from Aldrich Chemical Co. The ammonia (anhydrous) and monomethylamine (gas) were from Matheson.

3-Benzyloxypropionaldehyde (10-D) synthesis. 2.85 g of sodium hydroxide and 6.72 g of monochloroacetic acid were dissolved in water separately and then mixed. The solution was then mixed with 123 ml of benzyl alcohol and added to 100 ml of acrolein in a 500 ml flask dropwise. 30 ml of acetic acid was added to the flask and heated 80 hours at 40° C. The reaction was washed with water three times and dried with sodium sulfate. The product was obtained by distilling off the low boiling point fractions below 110° C. at reduced pressure (0.3 mmHg), 61 g, (31% yield) of 3-benzyloxypropionaldehyde (10-D) were obtained. NMR ($CDCl_3$): 9.67 (t, 1H, CHO, $J_{HH}=0.033$ Hz), 7.20 (s, 5 H, $C_6H_5$), 4.43 (s,2 H, $C_6H_5CH_2$), 3.73 (t. 2 H, $OCH_2$, $J_{HH}=3$ Hz), 2.60 (t of d, 2 H, $CH_2CHO$, $J_{HH}=3$ Hz, $J_{OH}=1$ Hz).

3-Benzyloxypropylidene diacetate (11-D) synthesis. 40 ml of acetic anhydride, 30 ml of ethyl ether and 3 ml of boron trifluoride/diethyl etherate were added to a 500 ml flask and 40 ml of 3-benzyloxypropionaldehyde was added to the flask in 5 minutes and stirred for another 10 minutes. The reaction mixture was washed with 200 ml of 10% sodium acetate and dried over sodium sulfate. The 3benzyloxypropylidene (11-D) was crystallized on standing at −13° C. and recrystallized with acetone and hexane as a colorless solid at 75% yield. NMR ($CDCl_3$) 7.67 (s, 5 H, $C_6H_5$), 6.90 (T, 1 H, $CH(OAc)_2$, $J_{HH}=3$ Hz), 4.47 (s, 2 H, $C_6H_5CH_2$), 3.73 (t,2 H, $OCH_2$, $J_{HH}=3$ Hz), 1.90-2.23 (m, 2 H, $CH_2CH$), 2.00 (S, 6 H, $CH_3$). Anal. Calcd. for $C_{14}H_{18}O_5$. C, 63.14; H, 6.81. Found: C, 63.44; H, 6.77.

3-Hydroxypropylidene diacetate (12-D) synthesis. 1 ml of 3-benzyloxypropylidene diacetate (11-D), 10 ml of ethylacetate, 0.1 g of 5% palladium-on-charcoal and 1 drop of perchloric acid were hydrogenolized at a pressure of 44 lb/inch² for 15 minutes. 0.5 g of calcium carbonate was shaken with the reaction mixture which was later filtered and then the solvent evaporated. The product (12-D) was obtained as a colorless oil which was quantitatively crystallized on standing at −13° C. NMR ($CDCl_3$): 6.84 (t, 1 H, CH(OAc), $J_{HH}=3$ Hz), 4.91 (s, 1 h, HO), 3.67 (t, 2 H, $HOCH_2m$ $J_{HH}=3$ Hz), 2.16-1.83 (m, 2 H, $CH_2CH$), 2.06 (M, 6 H, $CH_3$). anal. Calcd. for $C_7H_{12}O_5$. C, 47.72; H, 6.87. Found: C, 48.69; H, 6.80.

0 (3,3-Diacetatopropyl)-N,N-bis(2-chloroethyl) phosphoramidic chloride (14-D) synthesis. A mixture of 2 ml of compound 12-D and 2 ml of triethylamine was added dropwise to 1.32 ml of phosphorous oxychloride in 20 ml of dichloromethane at −20° C., and the mixture was stirred for 20 minutes and then stirred at room temperature for 1 hour and 40 minutes more. 2.516 g of bis(2-chloroethyl) amine hydrochloride was added to the mixture, and then 4 ml of triethylamine was added dropwise at −20° C. and stirred for 20 minutes. The mixture was continuously stirred for 1 hour and 40 minutes at room temperature. The reaction mixture was twice washed with water, once with phosphate buffer (pH, 7.0) and twice with water, and then dried over sodium sulfate. After removing the solvent, the product (14-D) was purified by column chromatography (ethylacetate : hexane - 1:1). 1.615 g of slightly yellow oil product was obtained, 29%. NMR ($CDCl_3$) 6.83 (t, 1 H, CH(OAc), JHH =3 Hz), 4.43-4.00 (q, 2 H, $OCH_2$, JHH =3 Hz, JOH =2.98 Hz), 3.77 (m, B H, $CH_2CH_2Cl$ ), 2.37-1.97 (m, 2 H, $CH_2CH$), 2.07 (S, 6 H, $CH_3$).

O-(3,3-Diacetatopropyl)-N,N-bis(2-chloroethyl) phosphorodiamide (15-D) synthesis. To 2.32 g of compound 14 was added 50 ml of 1 N ammonia in dichloromethane at −20° C. and the mixture was then stirred for 1 hour at room temperature. After the solvent was removed by evaporation, ether was added and the suspension was filtered. Ether was removed, and the residue was submitted to SiO$_2$ column chromatography and eluted with chloroform and acetone (1:1) to give 1.57 g of product 15, (71%), as a yellow oil which was crystallized on standing at $-13°$ C. NMR (CDCl$_3$) 6.88 (t, 1 H, CH(OAc)$_2$, JHH =3 Hz), 4.10 (q, 2 H, CH$_2$O, JHH =3Hz, JHH - 3 Hz), 3.3-3.8 (m, 10 H, CH$_2$CH$_2$Cl and NH), 2.0-2.3 (m, 2 H, CH$_2$CH(OAc)$_2$), 2.10 (s, 6H, CH$_3$). Anal. Calcd. for C$_{11}$H$_{21}$Cl$_2$N$_2$O$_6$P: C, 34.84; H, 5.58; N, 7.39. Found: C, 34.66; H, 5.44; N, 7.12.

0 (3,3-Diacetatopropyl)-N,N-bis(2-chloroethyl)-N$^1$-methylphosphorodiamide (16-D) synthesis. 3.5 ml of 3 N monomethylamine in dichloromethane at $-20°$ C. was added to 2.12 g of compound 14-D and stirred for 1 hour at room temperature. The other steps were the same as in making compound 15-D. 0.41 g of product (16-D) was obtained (20%) as a yellow oil. NMR (CDCl$_3$): 6.86 (t, 1 H, CH(OAc$_2$, JHH =3), 4.23-3.96 (Q, 2 H, OCH$_2$, JHH =3 Hz, JOH=3 Hz), 3.76-3.15 (m, 8 H, CH$_2$CH$_2$Cl), 2.78-2.43 (m, 4 H, CH$_3$NH), 2.18-1.95 (M, 2 H, CH$_2$CH(OAc)$_2$), 2.08 (s, 6 H, CH$_3$) Anal. Calcd. for C$_{12}$H$_{23}$Cl$_2$N$_2$O$_6$P: C, 36.65; H, 5.90; N, 7.13. Found: C, 36.59; H, 605; N, 7.30.

0 (3,3-Diacetatopropyl)-N,N-bis(2-chloroethyl)-N$^1$-ethylohosphorodiamide (17-D) synthesis. To 2.055 g of compound 14-D in 20 ml of dichlorom.ethane, 0.66 ml of ethylamine was added dropwise at $-20°$ C., and the mixture was stirred for 75 minutes at room temperature. The other steps were the same as for making compound 15-D. 0.97 g of product (17-D) was obtained (46%) as a yellow oil. NMR (CDCl$_3$) 6.83 (t, 1 H, CH(OAc)$_2$, JHH =3 Hz), 4.19-3.86 (q, 2 H OCH$_2$, JHH =3 Hz, JHH =3 Hz), 3.76-2.70 (m, 11 H, CH$_2$CH$_2$Cl and CH$_2$NH, 2.26-1.93 (m, 2 H, CH$_2$CH(OAc)$_2$, 2.10 (s, 6 H, CH$_3$), 1.26-0.98 (m, 3 H, CH$_3$CH$_2$NH). Anal. Calcd. for C$_{13}$H$_{25}$Cl$_2$N$_2$O$_6$P: C, 38.34; H, 6.19; N, 6.88. Found: C, 38.25; H, 6.20; N, 6.63.

0-(3,3-Diacetatopropyl)-N,N-bis(2-chloroethyl)-N$^1$,N$^1$-dimethylphosphorodiamide (18-D) synthesis. To a mixture of 1.066 g of compound 14-D and 0.27 g of dimethylamine hydrocholoride, 0.45 ml of triethylamine was added dropwise at $-20°$ C. This was then stirred for 2 hours at room temperature. The other steps were the same as in making compound 15-D. 0.42 g of product was obtained as a yellow oil which was crystallized on standing at $-13°$ C., 38%. NMR (CDCl$_3$) 6.80 (t, 1 H, CH(OAc)$_2$, JHH =3 Hz, 4.19-3.86 (q, 2 H, OCH$_2$, JHH =3 Hz, JOH =3 Hz), 3.70-3.06 (m, 8 H, CH$_2$CH$_2$Cl ), 2.73-2.56 (d, 6 H, (CH$_3$)$_2$N, JNH =% Hz), 2.26-1.96 (m,2 H, CH$_2$CH(OAc)$_2$), 2.05 (s, 6 H, CH$_3$). Anal. Calcd. for C$_{13}$H$_{25}$Cl$_2$N$_2$O$_6$P: C, 38.34; H, 6.19; N, 6.88. Found C, 37.91; H, 5.92; N, 6.47.

0 (3,3-Diacetatopropyl)-N,N-bis(2-chloroethyl)-N$^1$,N$^1$-diethylphosphorodiamide (19-D) synthesis. To 6.04 g of compound 14-D in 10 ml of dichloromethane, was added 0.31 ml of diethylamine dropwise at $-20°$ C. The mixture was stirred for 3 hours at room temperature. The other steps were the same as in making compound 15-D. 0.239 g of product (19-D) was obtained as a yellow oil, 36%. NMR (CDCl$_3$): 6.86 (t, 1 H, CH(OAc)$_2$, JHH =3 Hz), 4.20-3.86 (q, 2 H, OCH$_2$, JHH=3 Hz, JOH - 3Hz), 3.76-280 (m, 12 H, CH$_2$CH$_2$Cl and CH$_3$CH$_2$N, 2.29-1.98 (m, 2 H, CH$_2$CH(OAc)$_2$, 2.03 (s, 6 H, CH$_3$), 1.50 (t, 6 H, CH$_3$CH$_2$, JHH =3). Anal. Calcd.for C$_{15}$H$_{29}$Cl$_2$N$_2$O$_6$P: C, 41.39; H, 6.72; N, 6.44. Found: C, 41.59; H, 6.62; N, 6.24.

EXAMPLE 2

Further Synthesis of Aldophosphamide Analogs

Alterations of the reaction conditions shown in Example 1 were performed as follows to synthesize other analogs. See FIG. 4.

Figure 4:
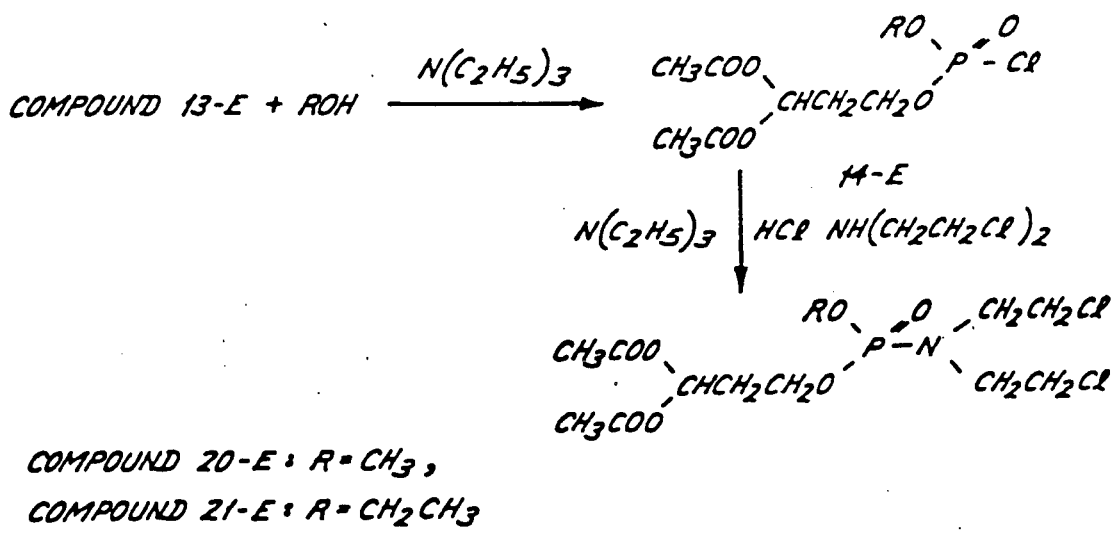
FIG. 4 further schematically shows a synthetic pathway for compounds of the present invention.

For the compounds 20-E and 21-E, the reaction sequence was altered. One equivalent of compound 12-D and triethylamine were added to 3 equivalents of phosphorus oxychloride. Instead of adding bis(2-chlorethyl)amine which would have produced compound (14-D), alcohol (ROH) (methanol or ethanol) and triethylamine were added to compound 13-D to produce compound 14-E. Then bis(2-chloroethyl)amine and triethylamine were added and compounds 20-E and 21-E were obtained by column chromatography (FIG. 4).

0 (3,3-Diacetatopropyl)-0-methyl-N,N-bis(2chloroethyl) phosphoramide (20-E synthesis. To 0.33 ml of oxyphosphorous chloride in 10 ml of dichloromethane, a mixture of 0.5 ml of 12 and 0.5 ml of triethylamine at $-20°$ C. was added dropwise, and stirred for 20 minutes and then for another 100 minutes at room temperature. A mixture of 0.2 ml of methanol and 0.5 ml of triethylamine was then added at $-20°$ C., and stirred for 20 minutes and then for another 100 minutes at room temperature. 0.5 g of bis(2-chloroethyl)amine hydrochloride and 1 ml of triethylamine were added, again at $-20°$ C., and stirred for 2 hours at room temperature. The other steps were as described in making compound 15-D. 0.189 g of product (20-E}was obtained as a yellow oil, 14%. NMR (CDCl$_3$), 6.86 (t, 1 H, CH(OAc)$_2$, JHH =3 Hz), 4.37-3.30 (m, 13 H, OCH$_2$, CH$_3$O and CH$_2$CH$_2$Cl), 2.26-2.06 (m, 2 H, CH$_2$CH(OAc)2, 2.03 (s, 6 H, CH$_3$). Anal. Calcd. for C$_{12}$H$_{22}$Cl$_2$N$_2$O$_7$P: C, 36.56; H, 5:63; N, 3.55. Found: C, 38.12; H, 5.92; N, 3.01.

0 (3,3-Diacetatopropyl)-0-ethyl-N,N-bis(2-chloroethyl)phosphoramide (21-E) synthesis. The steps and reagents were the same with synthesizing compound 20-E except 0.27 ml of ethanol instead of methanol was used. 0.692 g of product (21-E) was obtained as a yellow oil, 48%. NMR (CDCl$_3$): 6.84 (t, 1 H, CH(OAc)$_2$, JHH =3 Hz),4.43-3.26 (m, 13 H, OCH$_2$, CH$_3$CH$_2$ and CH$_2$CH$_2$Cl), 2.23-2.03 (m, 2 H, CH$_2$CH(OAc)$_2$), 2.06 (s, 6 H, CH$_3$) 1.36 (t, 3 H, CH$_3$CH$_2$, JHH =3 Hz). Anal. Calcd. for C$_{13}$H$_{24}$Cl$_2$N$_2$O$_7$P: C, 38.25; H, 5:93; N, 3.43. Found: C, 38.01; H, 6.10; N, 3.16.

EXAMPLE 3

Further Aldophosphamide Analog Synthesis

Figure 5:
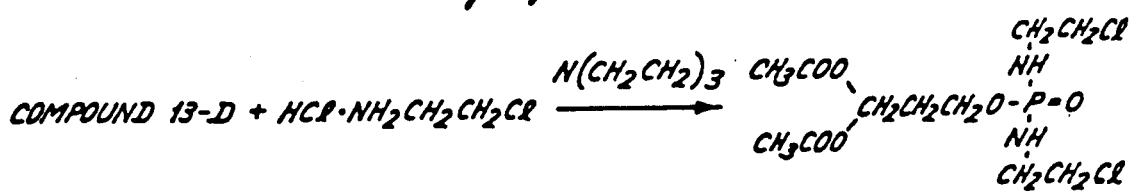
FIG. 5 schematically shows a synthetic scheme resulting in a compound of the present invention.

The modification as illustrated in FIG. 5 was used to produce compound 22-F.

0-(3,3-Diacetatopropyl)-N-(2-chloroethyl)-N-(2chloroethyl)phosphorodiamide (22-F) synthesis. To 0.66 ml of oxyphosphorous chloride in 20 ml of dichloromethane was added a mixture of 1 ml of compound 12-D and 1 ml of triethylamine at $-20°$ C. dropwise and stirred for 20 minutes, and the mixture was then stirred for another 100 minutes at room temperature. The other steps were as described in making compound 15-D (see FIG. 5). 0.32 g of product (22-F) was obtained as a yellow oil, 12% yield. NMR (CDCl$_3$) 6.89 (t, 1 H, CH(OAc)$_2$, JHH =3 Hz), 4.20-3.90 (q, 2 H, CH$_2$, JHH=3 Hz, JOH=3 Hz), 3.67-3.03 (m, 10 H, NH,NH and CH$_2$CH$_2$Cl), 2.26-2.00 (m, 2 H, CH$_2$CH(OAc)2). 2.06 (s, 6 H, CH3) Anal. Calcd. for C$_{11}$H$_{21}$Cl$_2$N$_2$O$_6$P: C, 34.84; H, 5.58; N, 7.37. Found C, 35.30; H, 5.88; N, 6.57.

Cyclohexylammonium Hydrogen N,N-di-(2-chloroethyl)phosphorodiamidate synthesis. 25 g of bis(2-chloroethyl)amine hydrochloride in 65 ml of oxyphosphorus chloride was heated to reflux for 12 hours. The excess oxyphosphorus was removed by evaporation. Di(2-chloroethyl)phosphoramidic dichloride was crystallized from petroleum ether and acetone (1:1). It was recrystallized 3 times with the same solvent. 14.5 g of white crystals were obtained, m.p. 54°–56° C. This melting point was the same as that previously reported. 3 g of di(2-chloroethyl)phosphoramidic dichloride and 1.15 g of phenol were added to 20 ml of toluene and heated to reflux, 1.85 ml of triethylamine was then added over 2 minutes, the reflux continued for 4 hours and then left overnight. The suspension was filtered and the filtrate was submitted to $SiO_2$ column chromatography (hexane:ethylacetate =7:3). Phenyl-di(2chloroethyl)phosphoramidic chloride was obtained as a yellow oil, 3.361 g, 92% NMR ($CDCl_3$) 7.3 (s, 5 H, $C_6H_5$), 3.87–3.33 (m, 8 H, $CH_2CH_2Cl$). 2.115 g of Phenyldi(2-chloroethyl) phosphoramidic chloride in toluene was bubbled with ammonia for 30 minutes. The precipitate was filtered and the solvent was removed by evaporation. The residue was diluted to cloudiness with petroleum ether and left overnight. Phenyl N,N-di(2-chloroethyl)phosphorodiamidate was crystallized, filtered, and without further purification, it was added to 50 ml of 100% ethanol and 0.4 g of platinum(IV) oxide and hydrogenolized for 15 minutes under the pressure 11 lb/inch$^2$. The mixture was filtered and 0.5 ml of cyclohexamine was added immediately. After the evaporation, the residue was washed onto a filter with ether. 0.501 g cyclohexylammonium hydrogen N,N-di(2-chloroethyl)phosphorodiamidate as an off-white powder was obtained, 23%, m.p. 124°–126° C.

EXAMPLE 4

Additional Aldophosphamide Analog Synthesis

Compounds B-8 to B-53 described in Table 1 were prepared by reaction of a precursor phosphoramidochloridate (compare FIG. 3, 14-D) or phosphorochloridate (compare FIG. 4 or FIG. 5) with the appropriate amine or alcohol by the methods described in Examples 1-3. Thus, compounds B-18 to B-25 and B-39 to B-53 were prepared by the methods described previously for compounds B-1 to B-7. The oxygen analogs B-26 to B-31 were prepared by the general procedure described for compounds B-8 and B-9. The phosphonate analogues B-33 to B-38 were prepared by the general method described below in Example 5.

EXAMPLE 5

Synthesis of: 0-(3,3-Diacetoxypropyl)-N,N-bis(2-chloroethyl)methylphosphonamidochloridate (B-10). A solution of 3-hydroxypropionaldehyde diacetoxy acetal (12-D) (0.5 g, 2.8 mmoles) in $CH_2Cl_2$ (5 mL) was added simultaneously with a solution of Et N (0.4 ml, 2.8 mmoles) in $CH_2Cl_2$ (3 mL), over a period of 30 min, to a stirred solution of methylphosphonic dichloride (378 mg, 2.8 mmoles) in $CH_2Cl_2$ (5 mL) maintained at −30° C. in a dry-ice/acetone cooling bath. After 30 min. the reaction mixture was warmed to room temperature and stirred for 2 h. It was then cooled again to −30° C. and N,N-bis(2-chloroethyl)amine hydrochloride (0.5 g, 2.8 mmoles) was added followed by $Et_3N$ (0.8 ml, 5.6 mmoles). After 30 min the reaction warmed to room temperature and stirred for a further 2 h. It was then washed with 0.45 M potassium phosphate buffer, pH 7.0 (20 mL) and $H_2O$ (20 mL ×2). The organic phase was dried over anhydrous $Na_2SO_4$. The solvent was evaporated and the remaining residue was submitted to flash chromatography on a column of silica using EtOAc-hexane (1:1, v/v) as eluent. Fractions (5 mL each) containing pure B-10 as evidenced by TLC analyses where combined and evaporated to give a viscous, pale yellow oil. It was dried in vacuo at 0.01 mm Hg over $P_2O_5$ for 48 h. Yield 456 mg (40%). $^1H$ NMR ($CDCl_3$): 6.92 (t, 1 H, $CH(OAc)_2$), 3.90–4.32 (m, 2 H $POCH_2$), 3.60–3.67(t, 4 H, 2 ×$CH_2Cl$), 3.34–3.40 (m, 4 H, 2 ×$NCH_2$), 2.02–2.10 (m, 2 H, $CHCH_2CH_2O$), 2.05 (s, 6 H, 2 ×O-$COCH_3$), 1.28 (d, J=16 Hz, 3 H, $CH_3$).

EXAMPLE 6

In Vitro Cytotoxicity of Compounds synthesized in Examples 1-3

Certain of the above referenced compounds were tested against L1210 lymphatic leukemia cells in vitro, the results being shown in Table 2. Cyclophosphamide (CF), ASTA Z 7557 and phosphoramide mustard (PM) were used as positive controls. The toxicity of compounds 16-D to 19-D to L1210 cells were about the same. This suggested that the cyclic intermediate structure may not be essential for the antitumor selectivity because compounds 16-D and 17-D can cyclize, at least theoretically, but 18-D and 19-D cannot, due to their chemical structure. That compounds 15-D to 19-D and 22 were more effective than compounds 20-E and 21-E suggested that a N at the R position was important for antitumor activity. All of the 8 compounds were at least as toxic as ASTA Z 7557 and more toxic than phosphoroamide mustard, indicating that the aldehyde intermediate may be important for the antitumor selectivity. Compounds 15-D and 22-F, the precursor of the two clinically important antitumor drugs, cyclophosphamide and ifosphamide, respectively were much more potent than ASTA Z 7557.

TABLE 2

| Compound No. | 15-D | 16-D | 17-D | 18-D | 19-D | 20-E | 21-E | 22-F | CP | ASTA | PM |
|---|---|---|---|---|---|---|---|---|---|---|---|
| ED$_{50}$ (microgram/ml) | 0.6 | 5.8 | 6.4 | 7.1 | 7.8 | 13.0 | 13.6 | 1.7 | 20 | 13.0 | 18.0 |

ED$_{50}$ was the concentration of drug that kills 50% of the cells. The compounds were incubated with L1210 lymphatic leukemia cells for 72 hr at 37° C. with the compound over the concentration range 0.5–20 microgram/ml. The viability of the cells was determined by a spectrophotometric assay.

Drugs were dissolved in sterile water and filtered through a 0.22 um (micrometer) filter (Millipore Corporation). The stock drug solutions were 1 mg/ml. 2 ×10$^4$ L1210 leukemia cells in 150 ul (microliter) RPMI 1640 medium complemented with 10% fetal calf serum were placed into every well of a 96 well plate. Drugs in 15 ul solution were then added and the cells were incubated for 72 hours at 37° C. 75 mg of 3-(4,5-dimethyL-thiazoL-2-yL)-2,5-diphenyL tetrazolium bromide (MTT) in 15 ul sterile water was added to each well and then incubated for 4 hours at 37° C. Acid-isopropanol (180 ul of 0.04 N HCl in isopropanol) was added to each well to dissolve the crystallized dye produced. The plates were read on a multiwell scanning spectrophotometer (ELISA reader) at a wavelength of 570 nm. The ED50 values were calculated.

EXAMPLE 7

Acetaldophosphamide: A Promising New Alternative to 4-Hydroperoxycyclophosphamide For The In Vitro Elimination of Leukemic Cells From Human Bone Marrow In vitro active cyclophosphamide derivatives such as 4-hydroperoxycyclophosphamide (4-HC) have been widely investigated for their potential to eliminate malignant cells from bone marrow prior to hematopoietic rescue following intensive chemotherapy. Studies of the present invention suggest that 4-HC is more active against human (myelogenous) leukemia cells than against normal granulocyte-macrophage progenitors (GM-CFC). Using long-term human marrow cultures, a sparing effect of 4-HC on GM-CFC ancestor cells was also observed. These differential drug sensitivities may be due to different intracellular levels of aldehyde dehydrogenase, a key enzyme in the deactivation of aldophosphamide (ALD); the latter is an important intermediate in the conversion of 4-HC to the presumed ultimate active metabolite, phosphorodiamidic mustard. In a search for new stable precursors to an compound B-1, (Table 1) was developed. The cytotoxic effects of compound B-1 on human normal GMCFC and leukemia colony forming cells (L-CFC) were determined in vitro using both prolonged (8 days) and short-term (0.5–4.0 hr) drug exposures (see Table 3). Compound B-1 was approximately 10-fold more potent than 4-HC on a molar basis. The IC$_{50}$ values (the drug concentrations required to reduce colony formation to 50% of controls) of compound B-1 for normal human GM-CFC were approximately 2-fold greater than those for the human myeloid cell line KBM-3 when assessed by continuous exposure. Interestingly, the IC$_{50}$ values for the GM-CFC after 1 hr drug exposure were 10-fold greater than those for the L-CFC. Thus, compound B-1 is more cytotoxic to KBM-3 leukemic clonogeneic cells than to normal GM-CFC cells and the differential appears most pronounced after short-term exposure to relatively high drug concentrations.

TABLE 3

| Cell type | IC$_{50}$ (ng/mL; range) | |
|---|---|---|
| | 1 hr exposure | 8 days exposure |
| Normal, GM-CFC | 1,000–1,500 | 45–55 |
| KBM-3, L-CFC | 100–200 | 20–25 |
| Ratio GM-CFC/L-CFC | 10 | 2 |

Experiments further delineating the differential cytotoxicities of compound B-1 in comparison to 4-HC and in combination with other drugs are in progress and are further confirming that compound B-1 is a promising new agent for the in vitro elimination of leukemic cells from bone marrow prior to autologous transplantation.

EXAMPLE 8

Cytotoxic Glycoside Derivatives

Figure 6:
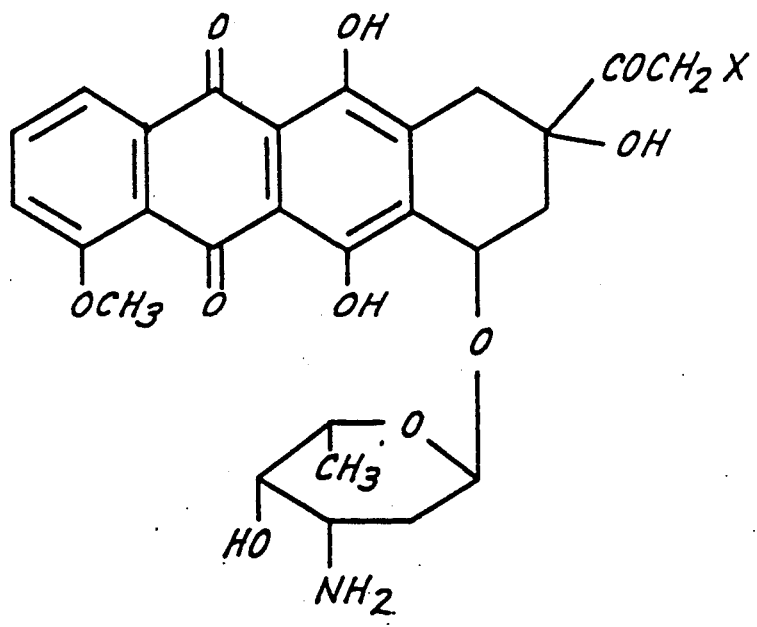
FIG. 6 schematically shows the structures of doxorubicin and daunomycin.

The cytotoxic glycoside antibiotics doxorubicin and daunomycin have the structures shown in FIG. 6. A number of bis(acyloxypropyl)phosphoramidates of the following general structure (C), where the R$^1$ group is doxorubicin or daunomycin bonded to the phosphorus through the sugar amino group, have been prepared.

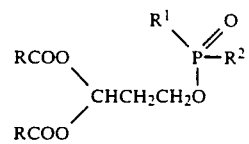

Table 4 shows the R, R$^1$ and R$^2$ substituents in structure C to produce compound No. C-1 to C-8.

TABLE 4

| Compound No. | R | R$^1$ | R$^2$ |
|---|---|---|---|
| C-1 | CH$_3$ | N-(3')-Doxorubicin | N(CH$_2$CH$_2$Cl)$_2$ |
| C-2 | CH$_3$ | N-(3')-Daunomycin | N(CH$_2$CH$_2$Cl)$_2$ |
| C-3 | CH$_3$ | N-(3')-Doxorubicin | NHCH$_2$CH$_2$Cl |
| C-4 | CH$_3$ | N-(3')-Daunomycin | NHCH$_2$CH$_2$Cl |
| C-5 | C(CH$_3$)$_3$ | N-(3')-Doxorubicin | N(CH$_2$CH$_2$Cl)$_2$ |
| C-6 | C(CH$_3$)$_3$ | N-(3')-Daunomycin | N(CH$_2$CH$_2$Cl)$_2$ |
| C-7 | C(CH$_3$)$_3$ | N-(3')-Doxorubicin | NHCH$_2$CH$_2$Cl |
| C-8 | C(CH$_3$)$_3$ | N-(3')-Daunomycin | NHCH$_2$CH$_2$Cl |

The preparation method for these compounds is described with respect to the prototype, N-[0-(3,3-diacetoxypropyl)-N,N-bis(2-chloroethyl)phosphorodiamido]-doxorubicin (C-1).

N,N-Diisopropylamine (0.032 mL, 0.2 mmoles) was added, with stirring, to a solution of doxorubicin free base (100 mg, 0.18 mmoles) in anhydrous chloroform/methanol (20:1) (15 ml). The mixture was cooled to −40° C. and 0-(3,3-diacetoxypropyl)]-N,N-bis(2-chloroethyl)phosphoramidochloridate (90 mg, 0.2 mmoles) in anhydrous dichloromethane (2 ml) was added. The reaction mixture was stirred for 30 min at −40° C., then at room temperature for 16 h. The solution was washed sequentially with an equal volume of 0.05 M phosphate buffer (pH 7) and water, and dried over MgSO$_4$. The solvent was evaporated and the residue was chromatographed on a column of silica using CHCl$_3$/MeOH (20:1 to 5:1) as eluent. The product was isolated as a red solid. Yield 23 mg (14%). NMR (CDCl$_3$/CD$_3$OD) 13.91 (s, 1 H, OH), 13.18 (s, 1 H, OH), 7.94 (d, J = 5 Hz, H-3), 7.72 (m, 1 H, H-2), 7.38 (d, J = 5 Hz, H-1), 6.93 (t, 1 H, CH(OAc)$_2$), 5.20 (d, J = 18 Hz, NHP), 4.7 (s, 2 H, CH$_2$OH), 4.01 (s, 3 H, OCH$_3$), 3.2–3.70 (m, 8H, 2 ×CH$_2$CH$_2$Cl), 2.01 (s, 6H, 2 ×)OAc), 1.06 (d, J = 4 Hz, 3H, CH$_3$).

The anticipated mechanism of activation of these compounds is shown in FIG. 7. As shown in Scheme 1, compound C is hydrolyzed to the aldehyde C-I by tissue carboxylate esterases. In normal cells, C-I is then oxidized by aldehyde dehydrogenase to the carboxylic acid, C-II, a chemically unreactive compound. However, in tumor cells, which are comparatively deficient in aldehyde dehydrogenase, C-1 undergoes an E-2 elimination reaction to give C-III. The latter compound, like phosphorodiamidic mustard, should be chemically reactive and form covalent adducts with target DNA.

Such differential metabolism should not only lead to higher levels of the cytotoxic moiety C-III in tumor cells compared to normal cells, but might overcome resistance to the parent anthracyclines (doxorubicin, daunomycin, etc.) arising from efficient cellular drug efflux (the multidrug resistance phenotype).

Growth inhibition of cultured L1210 leukemia cells was used as a measure of the relative cytotoxicities of the anthracycline derivatives of the present invention.

L1210 murine leukemia cells were maintained in vitro by serial culture in RMPI Medium 1640 containing 10% heat-inactivated fetal calf serum, L-glutamine (2 microM/ml), 2-mercaptoethanol (10 micro-M), penicillin (50 U/ml), streptomycin 50 micro-g/ml) at 37° C. in a humidified atmosphere of 5% $CO_2$ and 95% air. Cells in exponential growth at a density of $10^6$ cells/ml were exposed to varying drug concentrations for 1 h at 37° C. They were then harvested by centrifugation for 5 min at 1500 RPM, washed twice with ice-cold phosphate-buffered saline (2 ml), resuspended in drug-free medium at a concentration of $2 \times 10^5$/ml, and cultured for 72 h. Cell viability was determined by the MTT assay. (Mossman, T (1983). Rapid colorimetric assay for cellular growth and survival application to proliferation and cytotoxicity assays. J. Immunol. Meth. 65:55–63) The concentrations of drug inhibiting cell growth 50% ($IC_{50}$) is shown in Table 5.

TABLE 5

GROWTH INHIBITION OF L1210 LEUKEMIA CELLS IN VITRO BY DOXORUBICIN AND DAUNOMYCIN ANALOGUES[a]

| Compound | $IC_{50}$[b], (micromolar) |
|---|---|
| C-1) | 0.016 |
| C-2) | 0.018 |
| C-3) | 0.021 |
| C-4) | 0.025 |
| C-5) | 0.017 |
| C-6) | 0.020 |
| C-7) | 0.035 |
| C-8) | 0.030 |

[a]Exponentially growing cells were exposed to varying drug concentrations for 96 h at 37° C. The cells were then centrifuged, resuspended, and cultured in drugfree medium for 72 h.
[b]The drug concentration that inhibited cell growth by 50% compared to untreated control cultures.

EXAMPLE 9

Nucleoside Derivatives

Nucleoside analogues of the following general structure (D) were prepared as potential antitumor and anti-AIDS agents.

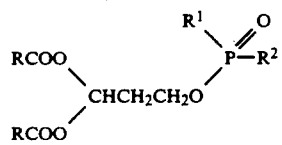

Table 6 shows the R, $R^1$ and $R^2$ substituents of structure D for compounds D-1 to D-4.

TABLE 6

NUCLEOSIDE DERIVATIVES SYNTHESIZED

| Compound No. | R | $R^1$ | $R^2$ |
|---|---|---|---|
| D-1 | $CH_3$ | $NH_2$ | 2',3'-dideoxyuridine-5'-yl |
| D-2 | $C(CH_3)_3$ | $NH_2$ | 2',3'-dideoxyuridine-5'-yl |
| D-3 | $CH_3$ | $NH_2$ | 5-methyl-2',3'-dideoxyuridine-5'-yl |
| D-4 | $C(CH_3)_3$ | $NH_2$ | 5-methyl-2',3'-dideoxyuridine-5'-yl |

The method of synthesis of these compounds can be illustrated with respect to the 2',3' dideoxyuridine derivative (D-1).

A solution of 1,2,4-triazole (132.23 mg, 1.92 mmole) and $POCl_3$ (98 mg, 60 ul, 0.639 mmoles) was dissolved in dioxane (2 mL) [dried over 4 Angstrom molecular sieves (300° C./1 h)]and a solution of triethylamine (267 uL, 1.92 mmole) in dioxane (1 mL) was added dropwise during a 45 min period. After stirring for an additional 40 min, the reaction mixture was filtered under nitrogen into a flask containing dideoxyuridine (90.4 mg; 0.426 mmoles) which has previously been evaporated with pyridine. After 30 min, a solution of 3-hydroxypropionaldehyde diacetoxy acetal (97.5 mg, 0.55 mmole) in dioxane (0.5 mL) was added. After stirring at room temperature for 5 hr the reaction mixture was concentrated to ⅓ of the starting volume and 1.3 mL of a 1.6 N solution of ammonia (2.13 mmole) in dioxane was added. After 30 min the reaction mixture was evaporated to dryness and the residue was taken up in the minimum volume of methanol and chromatographed on two thick layer (2 mm) plates (20×20) of silica. The product was isolated as a viscous colorless oil. Its NMR spectra was consistent with the assigned structure.

The effectiveness against growth of L1210 cells of 1 these nucleoside analogs was tested and the growth inhibition shown in Table 7.

TABLE 7

GROWTH INHIBITION OF L1210 LEUKEMIA CELLS IN VITRO BY NUCLEOSIDE ANALOGUES[a]

| Compound | $IC_{50}$[b], micro-M |
|---|---|
| D-1) | 1.4 |
| D-2) | 0.7 |
| D-3) | 1.3 |
| D-4) | 1.6 |

[a]Exponentially growing cells were exposed to varying drug concentrations for 96 h at 37° C. The cells were then centrifuged, resuspended, and cultured in drugfree medium for 72 h.
[b]The drug concentration that inhibited cell growth by 50% compared to untreated control cultures.

EXAMPLE 10

Predicted Mechanism of Activation

The anticipated mechanism of activation of these compounds is shown in FIG. 8. Scheme 2 shows that compound G (where $R_1$ is a cytotoxic moiety) is converted to the aldehyde G-I by tissue esterases. In normal cells, G-I is preferentially converted to the carboxylic acid, G-II, by aldehyde dehydrogenase. G-II should be chemically stable and biologically inert. In tumor cells, however, G-I should undergo E-2 elimination to give the phosphorodiamidate, G-III. This compound will then be converted to the corresponding phosphate, G-IV, by spontaneous chemical or enzymatic hydorlysis. Such differential metabolism should lead to higher levels of the $R^1$ cytotoxin such as a cytotoxic mustard, adriamycin or nucleotide analogue, G-IV, in tumor cells.

EXAMPLE 11

Suitability of a New Stable Acetal Analogue of Aldophosphamide for Purging Leukemic Cells From Bone Marrow In vitro chemotherapy of bone marrow with the aim of selectively eliminating tumor cells prior to autologous marrow transplantation is currently being introduced into clinical practice as a means of improving the treatment for acute leukemia. Numerous drugs have been proposed for this purpose based on preclinical models (Sharkis et al., 1980; Korbling et al., 1982; Herve, et al., 1983; Glasser et al., 1983; Hagenbeek and Martens, 1984; Stiff et al., 1984; Ciobanu et al., 1986). The most extensively used compounds 15 to date are the cyclophosphamide derivatives 4-hydroperoxycyclophosphamide (4-HC) and mafosfamide. 4-HC was initially studied by Sharkis and co-workers in a rodent acute leukemia model. 4-HC selectively eliminated leukemic cells from contaminated bone marrow yet permitted hemopoietic reconstitution when the manipulated marrow was infused into lethally irradiated hosts (Sharkis et al., 1980). Subsequently, 4-HC was introduced for the clinical use in humans. The early results are very encouraging and autologous transplantation with in vitro treated marrow holds promise of substantially prolonging the duration of second and third remissions in patients with acute myeloid leukemia (Kaizer et al., 1985; Yeager et al., 1986). Similar results have been reported after autologous transplantation with marrow treated with mafosfamide (Gorin et al., 1986; Korbling et al., 1986). Both 4-HC and mafosfamide give rise in solution to 4-hydroxycyclophosphamide, an unstable compound that spontaneously breaks down to yield the cytotoxic alkylating moiety, phosphorodiamidic mustard (Sladek and Landkamer, 1985). Although the in vitro antileukemic selectivity of these cyclophosphamide derivatives against human leuklemic cells is somewhat controversial (Delforge et al., 1982; Kluin-Nelemans et al., 1984), the clinical results favor their use. .

In an attempt to increase the efficacy of this general class of compounds, a series of bis(acetoxy)acetal analogues of aldophosphamide and aldoifosfamide, have been synthesized compounds that are activated by cellular carboxylate hydrolases. The in vitro cytotoxicity of the most potent of these compounds, acetaldoifsphamide, was studied on human myeloid leukemic and normal clonogenic cells. On a molar basis, is 8–10 times more potent than 4-HC against leukemic cells. Importantly, it retained pronounced activity against leukemic cells that were highly resistant to the anti-leukemic agents m-AMSA and doxorubicin.

Short-term suspension cultures were used to evaluate the early recovery of committed myeloid stem cells (GM-CFC) proliferation after exposure of bone marrow to increasing concentrations of. Considerable variation was observed between individual marrow samples. Following exposure to drug concentrations that abolished 95–100% of detectable GM-CFC, there was typically a 24-hour delay in proliferation of the GM-CFC pool. During the following two to three days it expanded with doubling times of a mere 6–12 hours. These recovery kinetics are similar to those observed after bone marrow incubation with 4-HC, but different from that observed after bone marrow exposure to an intercalating agent or ionizing radiation. Long-term suspension cultures (LTSC) of normal bone marrow were used as a model of autologous transplantation to study the continued GM-CFC production over several weeks. After incubation with at a concentration that abolished more than 99% of detectable GM-CFC, the marrow was seeded on previously established autologous feeder layers. GM-CFC recovery to control levels occurred in two to three weeks and remained constant for the remainder of the five-week observation period.

To simulate remission bone marrow, normal marrow cells were mixed with myeloid leukemic cells (cell line KBM-3) in 95:5 proportion. The mixture was treated with and LTSC were established. Again, GM-CFC increased to control levels within three weeks, but leukemic cell proliferation was not evident. We conclude that , which is stable in saline solution and easy to handle, is an alternative to 4-HC for the selective elimination of myeloid leukemic cells from bone marrow prior to autologous transplantation.

Materials and Methods

Drugs

The used acetaldoifosphamide in this investigation was synthesized and characterized as described in ealier examples.

Figure 2:
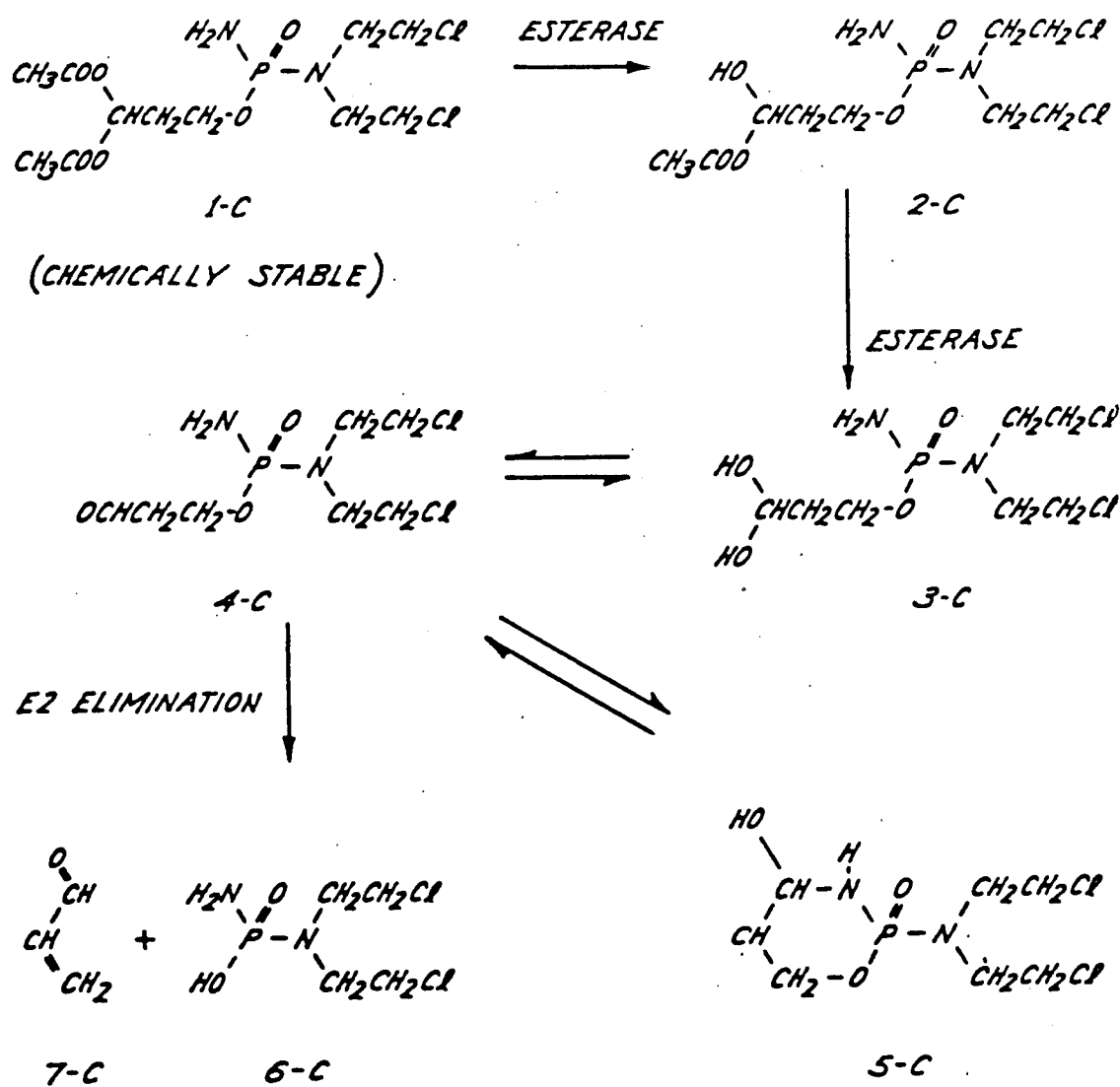
FIG. 2 schematically shows the activation pathway for compounds of the present invention.

The chemical structure of acetaldoifosphamide (1-C) is shown in FIG. 2. When dissolved in phosphate-buffered saline (PBS) (pH 7.4), at room temperature, the compound has a half-life greater than 80 hours. Its proposed mechanism of activation is also shown in FIG. 2. Sequential cleavage of the acetate linkages of C-1 by carboxylic esterases yields the aldehyde hydrate, 3-C. Loss of water from the latter yields the free aldehyde, 4-C, which exists in equilibrium with the cyclic tautomer, 4-Hydroxycyclophosphamide, (5-C). Spontaneous degradation of the compound 4-C or 5-C by an E2 elimination mechanism generates the active alkylating moiety, ifosphoramide mustard, 6-C, and acrolein, 7-C. Alternatively, through the action of cellular aldehyde dehydrogenase, aldoifosphamide may be biotransformed to carboxyifosphamide, a comparatively inactive product.

In the initial experiments, acetaldoifosphamide (1-C) was weighed and dissolved in Dulbecco's phosphate-buffered saline (pH 7.4) (GIBCO, Grand Island, N.Y.) supplemented with Ca++ (10 mg %) and glucose (100 mg %) (enriched PBS) immediately prior to each experiment. When stored frozen at −80° C. as a stock solution of 265 uM, the drug retained full cytotoxic activity for more than four months. In subsequent experiments a frozen stock solution was used; aliquots were thawed as necessary immediately prior to use.

4-HC was a generous gift of ASTA Werke, Bielefeld, Federal Republic of Germany. It was dissolved in enriched PBS immediately prior to use. Ficoll was purchased from Pharmacia Fine Chemicals (Piscataway, N.J.) and diatrizoate sodium was obtained as a 50% (w/v) solution from Winthrop Laboratories (New York, N.Y.)

Bone Marrow

Normal bone marrow was obtained from four different volunteers. The marrow samples were diluted in 1 ml of PBS containing 1,000 IU preservative-free heparin (Fisher Scientific, Fairlawn, N.J.). The mononuclear cell fraction was isolated on a Ficoll-Diatrizoate gradient (density 1.080 g/cm$^3$.

Cell Lines

The human myeloid leukemic cell ine KBM-3 was established from a patient with acute myeloid leukemia. Sublines of KBM-3 were made resistant to the intercalating agents m-AMSA (KBM-3/AMSA) and doxorubicin (KBM-3/DOX). The cells used in the present study were 100 to 130-fold resistant either to m-AMSA or to doxorubicin as determined by clonogenic assay.

HL-60 cells (Gallagher et al., 1979) were generously provided by Dr. R. Gallo at the National Cancer Institute (Bethesda, Md.). The HL-60/AMSA cell line was developed as previously reported (Odaimi et al., 1986; Beran and Andersson, 1987); the passages used in the present studies were about 70-fold resistant to m-AMSA. All cell lines were maintained in suspension in plastic tissue culture flasks (Corning Glass Works, Corning, N.Y.) in Iscove's modification of Dulbecco's minimum essential medium (IMDM, GIBCO Laboratories, Grand Island, N.Y.) supplemented with 10% heat-inactivated fetal calf serum (FCS, Irvine Scientific, Santa Ana, Calif.). The cells were divided to $3-5 \times 10^5$ per ml twice weekly and supplemented with fresh medium. All cell lines were split 24–48 hours prior to use.

Short-term cultures of clonogenic leukemic cells and committed normal human granulocyte-macrophage progenitor cells Low density normal mononuclear bone marrow cells (1.080 g/cm$^3$) were enriched on Ficoll-diatrizoate. The mononuclear fraction obtained in this manner contained the pluripotent stem cells and the committed myeloid stem cells (GM-CFC) The cells ($1 \times 10^5$ per ml) were cultured in 35-mm Petri dishes (Costar, Division of Data Packaging Corp., Cambridge, Mass.) in IMDM supplemented with 20% FCS and, as viscous support, 0.3% agar, using amodification of the method of Pike and Robinson (1970). Colony stimulating factor (CSF) was obtained from human placenta (HPCM) as described by Burgess et al. (1977). Five to twenty percent (v/v) HPCM was incorporated in a "feeder" layer of 1 ml IMDM with 20% FCS and 0.5% agar; the feeder layer was allowed to solidify at room temperature prior to the addition of the cells in a 1 ml overlayer. After incubation for 8 days at 37° C. in a fully humidified atmosphere of 5% CO$_2$ and 12% O$_2$ balanced with N$_2$ to 100%, colonies (clones with more than 50 cells) were counted under an inverted phase-contrast microscope. The leukemic cell lines were cloned in vitro under the same conditions as normal bone marrow BM-CFC, except that exogenous colony stimulating factor was omitted. This technique permitted the identification of leukemic CFC when culturing a mixture of leukemic cells and normal bone marrow.

Cytotoxicity of Acetaldoifosphamide and 4-HC to Normal and Leukemic cells.

Normal mononuclear bone marrow cells or leukemic cells in enriched PBS (pH 7.4, supplemented with glucose, Ca++, and 5% FCS), were incubated with the respective drug over a range of concentrations. Cells incubated simultaneously in drug-free medium served as controls. After incubation, the cells were washed with ice-cold PBS and pelleted by centrifugation for 10 min at 150 × g; this procedure was repeated. The cells were then resuspended in IMDM to the desired final concentration and used for in vitro cultures.

To examine the cytotoxicity of acetaldoifosphamide to leukemic cells resistant to m-AMSA and doxorubicin, the drug, the agar-medium, and the cells were mixed immediately prior to plating in Petri dishes. After 8 days, the surviving clonogenic cells were counted as described above. The surviving fraction was calculated by comparing the number of colonies formed after drug exposure with the number formed after incubation of the cells in drug-free medium. Survival curves were constructed, and IC$_{50}$ and IC$_{90}$ values (the drug concentrations that inhibited colony formation by 50% and 90%, respectively) were determined A "cross-resistance index" was calculated by comparing the IC$_{50}$ values of the intercalator-resistant cell lines with that of the parent, sensitive cell line.

Long term suspension cultures

A modification of previously reported techniques was used (Gartner and Kaplan, 1980; Greenberg et al., 1981; Potter et al., 1981; Coulombel et al., 1983). Briefly, $1 \times 10^7$ mononuclear bone marrow cells were suspended in 10 ml IMDM supplemented with 12.5% horse serum, 12.5% FCS and $5 \times 10^{-6}$ M hydrocortisone succinate (HyC) (Abbott Laboratories, N. Chicago, Ill.) in 25 cm$^2$ tissue culture flasks (Corning Glass Works, Corning N.Y.). After 8 to 10 days an adherent fibroblast (feeder) layer, supplying a hemopoietic microenvironment, was established. The non-adherent cells were washed off, and the feeder layer was irradiated with 3.0 Gy gamma-irradiation at a dose rate of 3.3 Gy per min. A second bone marrow sample was obtained from the same donor, and low-density mononuclear cells were isolated as above. The cells were exposed for 60 min at 37° C. to increasing drug concentrations. After two washings, the cells were suspended in 10 ml IMDM with 10% FCS and $5 \times 10^{-6}$ M HyC, and then added to the previously established feeder layers. All cultures were established in duplicate, and all flasks were incubated for five weeks at 37° C. in an atmosphere of 5% CO$_2$ and 12% O$_2$ balanced with N$_2$ to 100%. Twice weekly, 85% of the medium was replaced with fresh medium. Immediately after drug exposure, and at weekly intervals up to 5 weeks, one ml of the cell suspension was removed and monitored for the presence of GM-CFC using the soft agar assay as described above. The total number of surviving GM-CFC formed from untreated cells served as a quality control of the culture system and as a reference (positive controls) for calculating the surviving GM-CFC fraction in cultures of drug-treated cells Flasks containing irradiated stromal cell layers alone were subjected to the same twice-weekly media changes and were monitored weekly for possible regrowth of GM-CFC (negative controls). After five weeks, all non-adherent cells were removed from the flasks. The feeder layers were carefully rinsed twice with 10 ml of PBS, then treated with 0.2% trypsin in EDTA solution (GIBCO Laboratories, Grand Island, N.Y.) for 2–3 min at 37° C. After washing, the resulting single cell suspensions were assayed for GM-CFC.

In two separate experiments, KBM-3 cells ($5 \times 10^5$ leukemic cells/flask) were mixed with normal bone marrow in 5:95 ratio prior to treatment with (39.6 uM for 60 min at 37° C. to simulate in vitro chemotherapy of "remission" bone marrow. These cultures were monitored weekly for the presence of GM-CFC and leukemic CFC as described above.

Short Term Suspension Culture

The kinetics of early GM-CFC recovery after exposure of bone marrow to was studied in short term suspension cultures. Light density bone marrow cells ($5 \times 10^6$/ml) were exposed to the drug for 60 min at 37° C. as described above. For comparison, some cell samples were treated with another cell cycle non-specific drug (m-AMSA, 3.0 or 4.0 uM). After incubation with drug or PBS, the cells were washed twice and resuspended to a concentration of $10^6$ per ml in IMDM supplemented with 12.5% FCS, 12.5% horse serum and $5 \times 10^{-6}$ M HyC. Some samples were also treated with gamma-irradiation, 3.0 or 3.5 Gy, or mixed with irradiated cells (10 Gy) in a 1:99 ratio. The dose rate used was 3.3 Gy/min. Aliquots of 10 ml each were then incubated in 25 cm² tissue culture flasks at 37° C. in a fully humidified atmosphere of 5% $CO_2$ in air. Eighty-five percent of the media was changed on days four and seven of the incubation period. At regular intervals up to day 10, 0.2-0.5 ml samples were reaoved and assayed for GM-CFC. Duplicate flasks were used for treated and untreated cells.

Results

Survival as a function of drug concentration

Exposure of bone marrow cells to acetaldoifosphamide or 4-HC in increasing concentrations for 60 min resulted in a concentration-dependent GM-CFC kill; the surviving fraction was exponentially related to the concentration (FIG. 9A). On a molar basis, acetaldoifosphamide was 8 to 10 times more cytotoxic than 4-HC. Little interindividual variation between different marrow samples was observed when all erythrocytes were carefully separated from the sample prior to the incubation. Both drugs were more active against normal marrow GM-CFC than against leukemic myeloid CFC (cell line KBM-3) (FIG. 9B).

Figure 10:
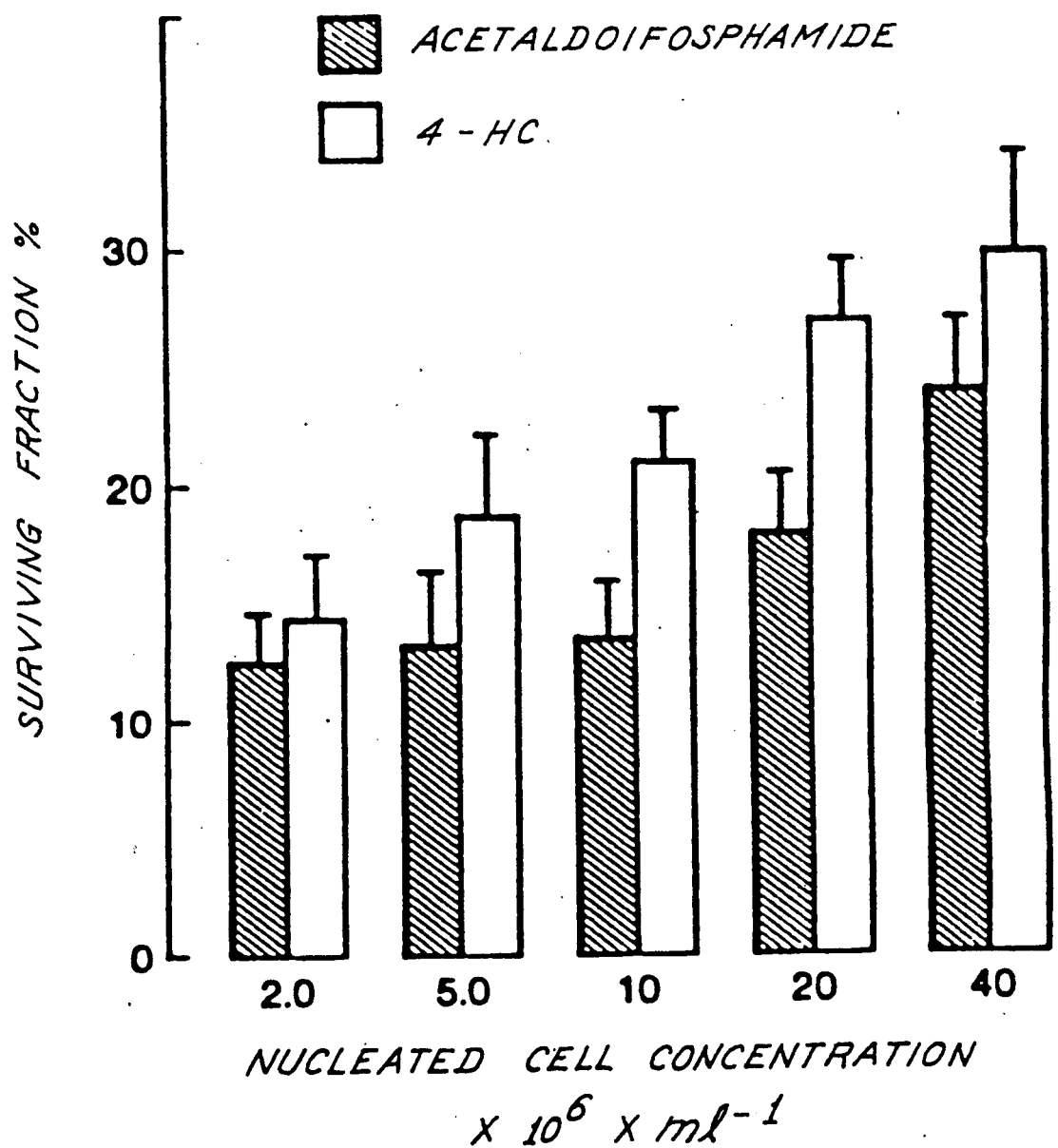
FIG. 10 shows the effect of increasing cell concentration on the cytotoxicity of acetaldoifosphamide and 4-HC to human KBM-3 cells. All determinations were performed in triplicate in two separate experiments (Bars ±S.D.).

For a given concentration of acetaldoifosphamide, the nucleated cell concentration influenced the survival. Thus, at a drug concentration of 1.3 uM (approximately $IC_{90}$), a 2-fold increase in clonogenic KBM-3 cell survival was evident over a 20-fold increase in cell concentration. Similar cell concentration dependence was observed for the cytotoxicity of 4-HC (FIG. 10).

Effect of on cells resistant to doxorubicin or m-AMSA

Figure 11:
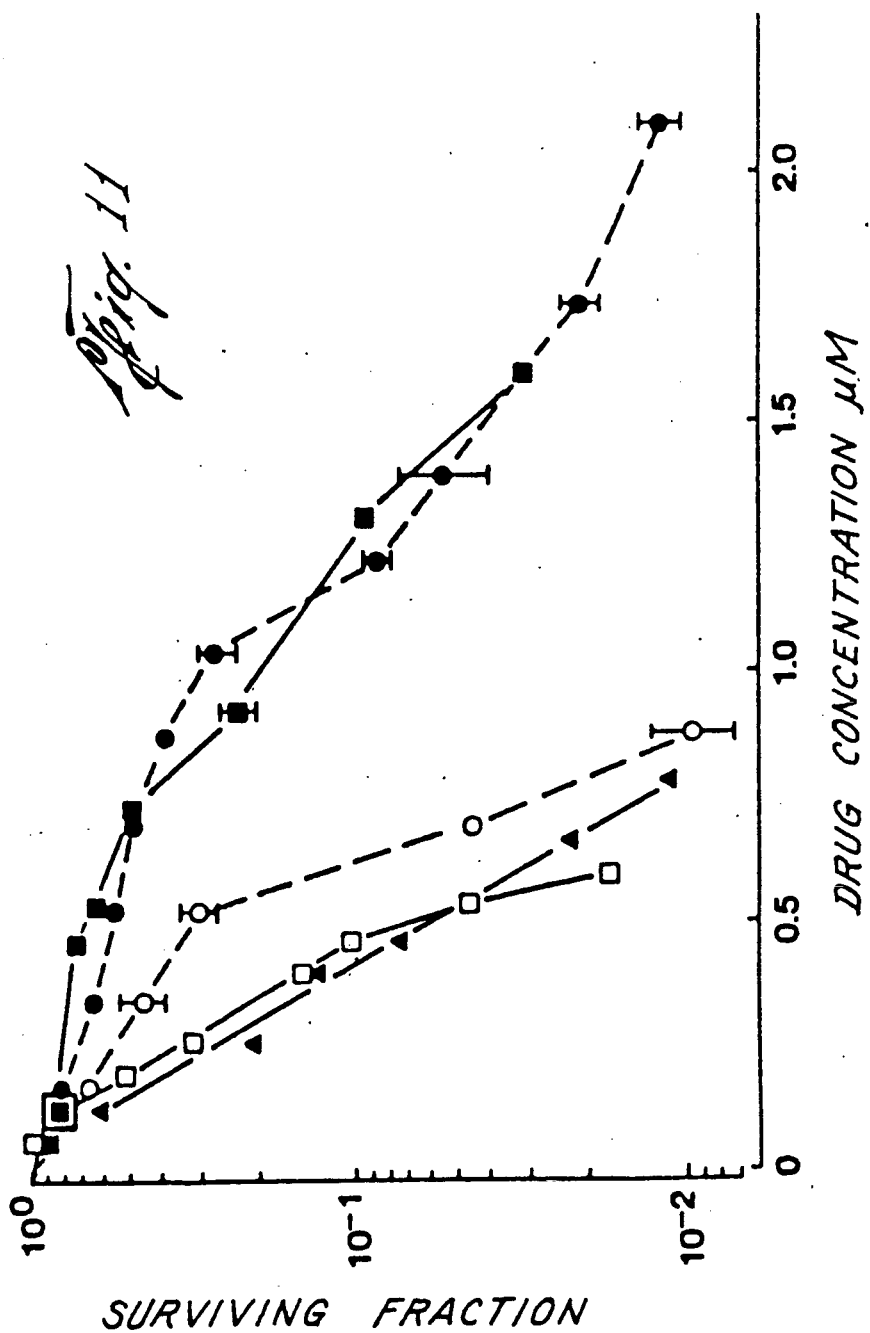
FIG. 11 shows comparative cytotoxicity of acetaldoifosphamide to the human myeloid cell lines KBM-3 and HL-60 All cells were plated at $5 \times 10^3$ per ml. The drug was incorporated into the medium-agar cell mixture to allow for prolonged cellular drug exposure with the detection of a low degree of cross-resistance. (Open squares) KBM-3; (solid square) KBM-3/AMSA; (solid triangles) KBM-3/DOX; (open circles) HL-60; (solid circles) HL-60/AMSA.

The sensitivity of leukemic clonogenic cells from the human myeloid lines KBM-3 and HL-60 to acetaldoifosphamide was compared to that of sublines with 70-fold (HL-60/AMSA) and 130-fold (KBM-3/AMSA) resistance to m-AMSA, and to that of a subline of KBM-3 (KBM-3/DOX) with 100-fold resistance to doxorubicin. (FIG. 11 and Table 8). The survival curves indicated exponential kill for all cell types. Comparison of the $IC_{50}$ and $IC_{90}$ values revealed a total absence of cross-resistance between acetaldoifosphamide and doxorubicin in doxorubicin-resistant cells. The two m-AMSA-resistant cell lines were marginally less sensitive to acetaldoifosphamide than to m-AMSA.

Figure 12:
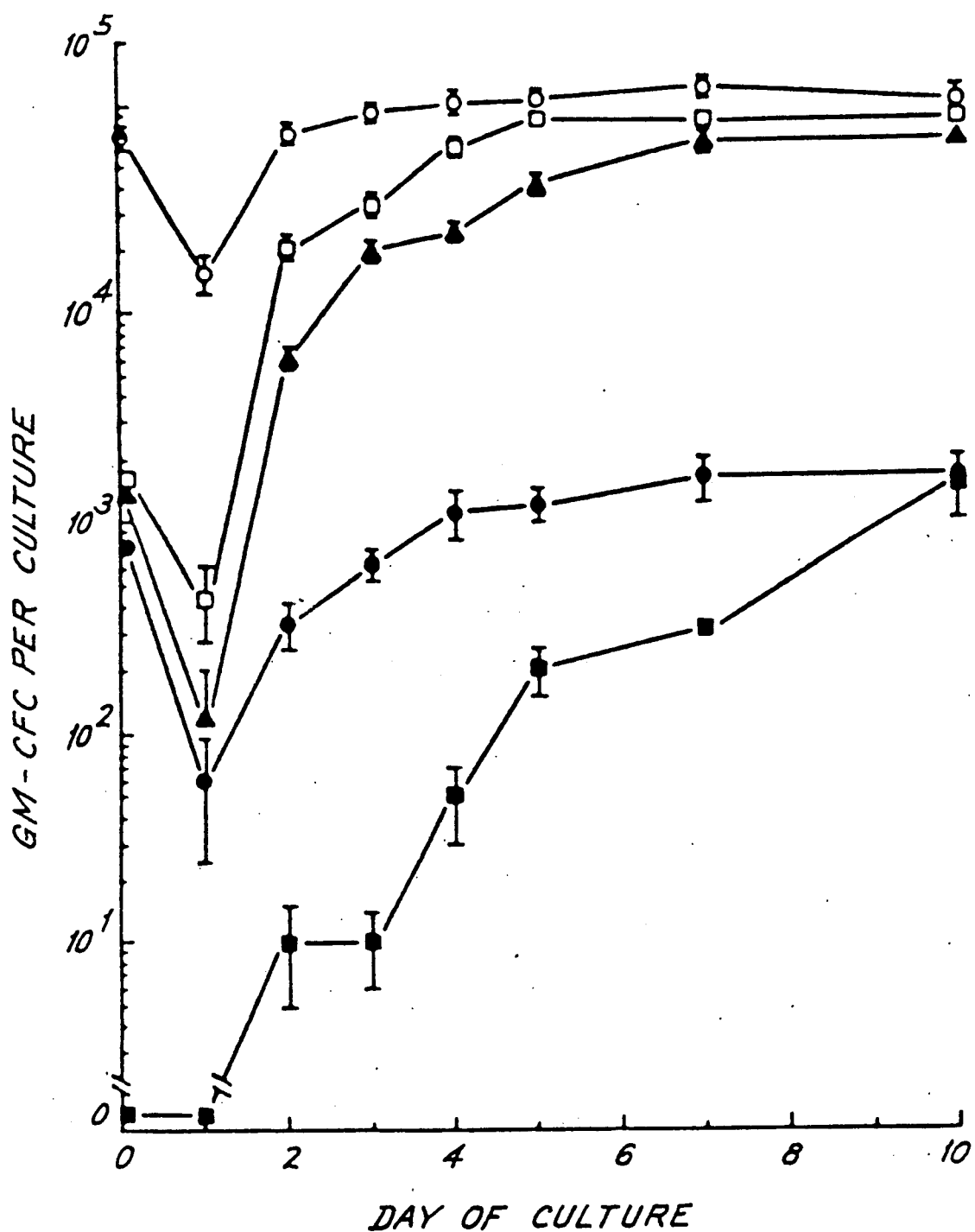
FIG. 12 shows short-term (10 days) suspension culture of normal human bone marrow (NBM) after 60 min exposure to PBS. $10^7$ cells (open circles), $10^5$ cells mixed with $10^7$ irradiated cells (solid circles) (10.0 Gy), or to acetaldoifosphamide acetaldoiphosphamide at 26.4 uM (open squares), or 39.6 uM (solid squares), or to 4-HC at 104 uM (solid triangles). Drug exposure was at 37° C., $5 \times 10^6$ cells per ml, final voluumn =2 ml. After washing twice, the cells were seeded at $10^6$ cells/ml. Each point is the mean of triplicate GM-CFC determinations from two separate cultures.
Figure 13:
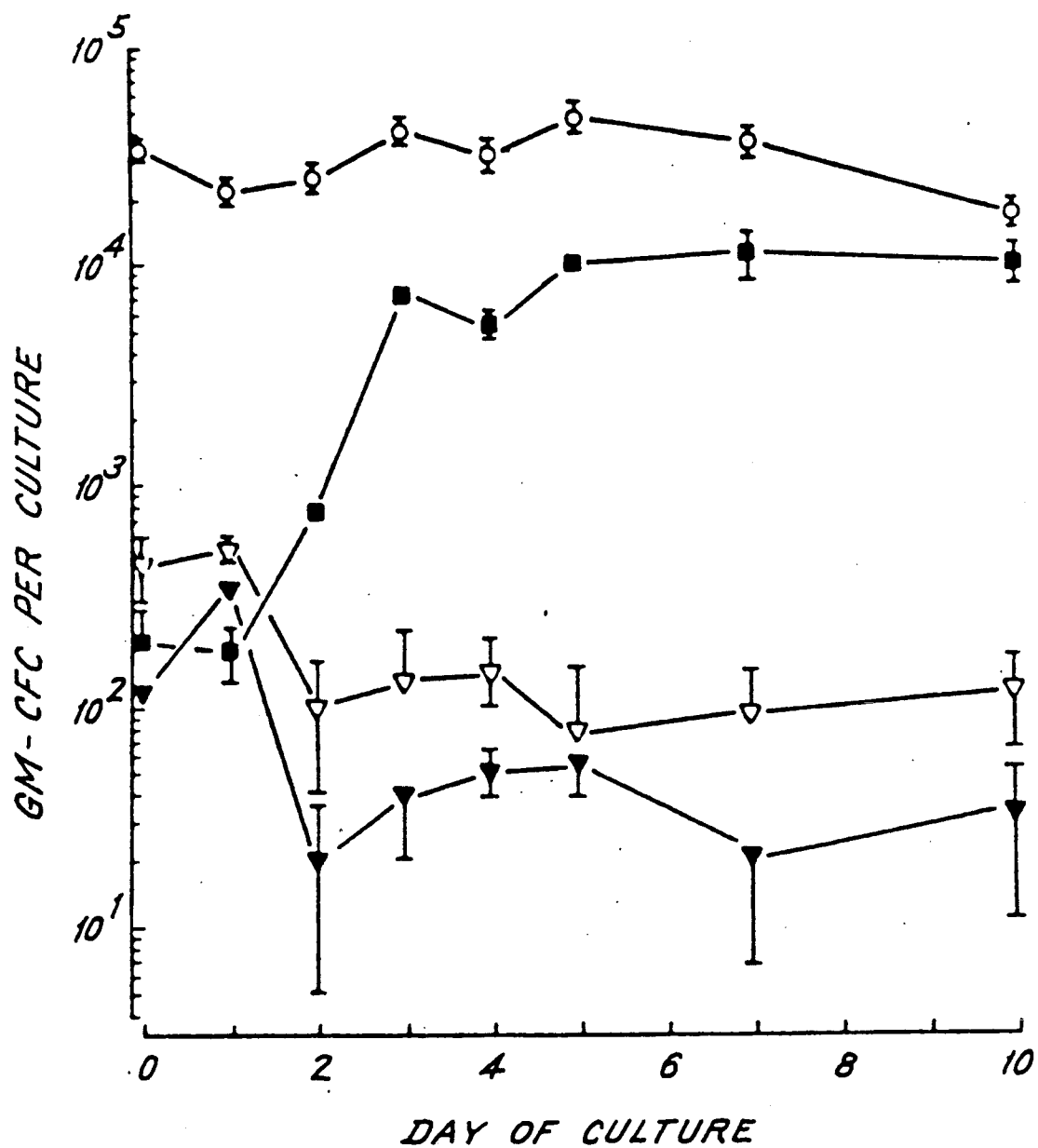
FIG. 13 shows comparison of the regrowth of GM-CFC in short-term suspension cultures of normal human bone marrow exposed to acetaldoifosphamide 39.6 uM (solid squares), or m-AMSA 3.0 uM (open triangles), or m-AMSA 4.0 uM (solid triangles); cells incubated in PBS (open circles) served as controls. $5 \times 10^6$ cells/ml (total volume 2 ml) were exposed to drug for 60 min at 37° C. and, after washing, seeded in suspension at $10^6$ cells/ml. Each point is the mean of triplicate GM-CFC determinations from two separate cultures.
Figure 14:
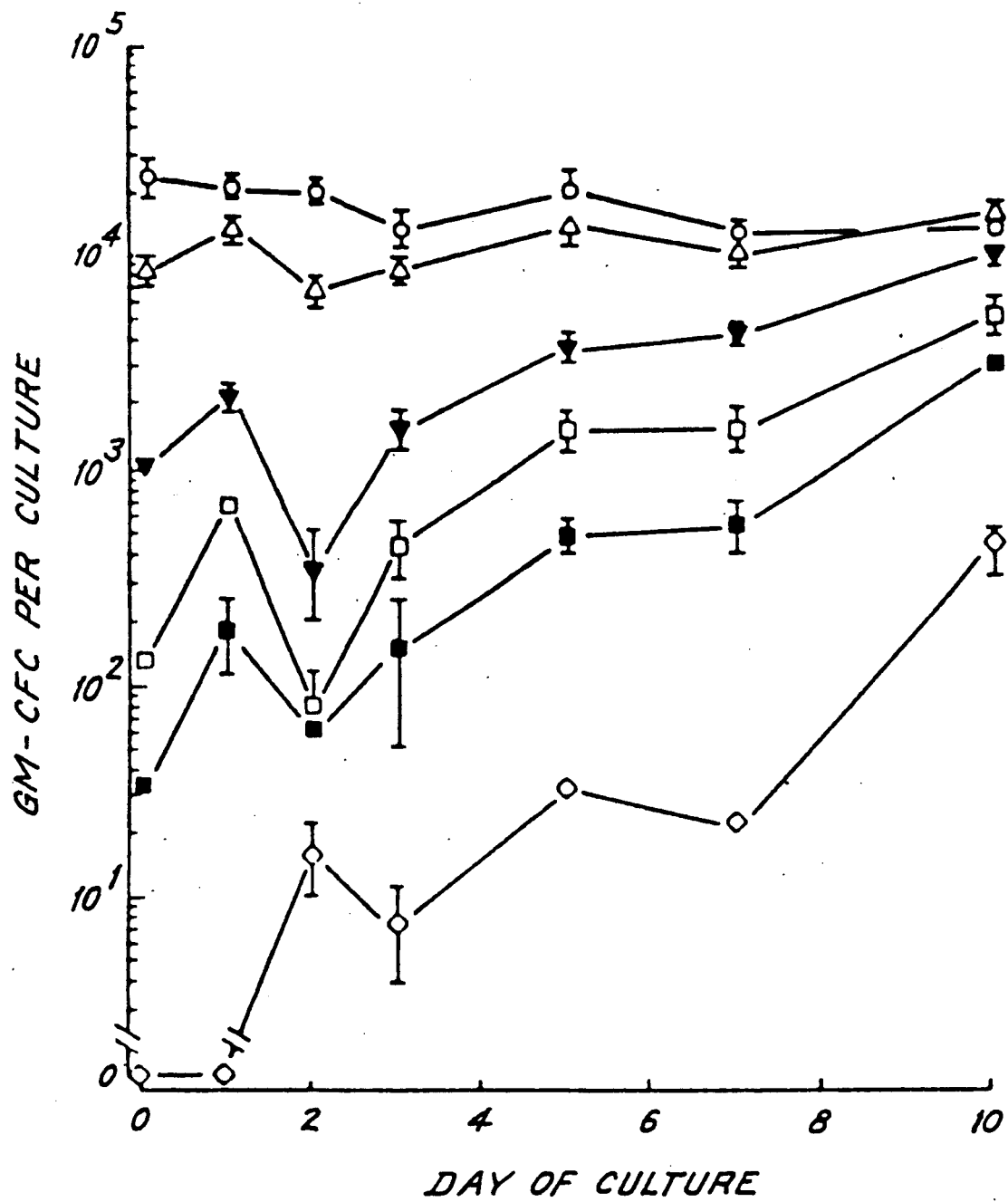
FIG. 14 shows regrowth of GM-CFC from normal bone marrow in short-term suspension cultures after 60-min exposure to increasing concentrations of acetaldoifosphamide. Each point is the mean of triplicate determinations from two separate cultures. Controls (open circles), 13.2 uM (open triangles), 26.4 uM (solid triangles), 33.0 uM (open squares), 39.6 uM (solid squares), 53 uM (open tilted squares).

Early regeneration kinetics of GM-CFC from drug-treated bone marrow in short term suspension cultures Little fluctuation in the GM-CFC growth was observed in untreated culture during the 10-day observation period in the flasks that were seeded with 10⁶ cells per ml or 10⁴ cells per ml followed by 10⁶ irradiated cells per ml (FIG. 12). GM-CFC recovery in bone marrow treated with different concentrations of is shown in FIGS. 12-14. Considerable heterogeneity in the proliferative pattern of individual marrow samples was evident over the first 48 hours after drug exposure. In two experiments, a triphasic GM-CFC growth pattern was observed: an early plateau or decline over the first 24 hours, followed by a proliferative surge over the ensuing 2 to 4 days, then a final expansion phase (FIGS. 12 and 13). Somewhat different recovery kinetics were observed in a third experiment (FIG. 14). Here, the GM-CFC pool expanded rapidly over the first 24 hours with a slight decline at two days followed by steady expansion over the next eight days of observation. The culture exposed to the highest concentration of initially had no detectable GM-CFC, however after day two rapid GM-CFC proliferation was apparent.

The GM-CFC proliferated with a doubling time of 6 to 12 hours; this is similar to the recovery kinetics observed after treatment of bone marrow with high-dose 4-HC (FIG. 12) but different from that observed after treatment with ionizing radiation (not shown) or m-AMSA (FIG. 13), both of which exhibit nonselective killing of mature (GM-CFC) and primitive (pluripotent) myeloid progenitor cells.

Regeneration of GM-CFC from drug-treated bone marrow in lonq-term cultures

The absolute number of GM-CFC in the control cultures (marrow without drug treatment) declined by about 30% weekly over the observation period. After bone marrow exposure to acetaldofosphamide the GM-CFC proliferation was biphasic (Table 9) with rapid recovery to control level by 2 weeks. The rate of recovery was inversely related to the drug concentration up to 39.6 uM. During the final three weeks of culture the GM-CFC proliferation rate was similar to that of the controls. In flasks containing only irradiated feeder layers (negative controls), GM-CFC production was not detectable after the first week of observation (Table 9). The radiation dose of 3.0 Gy did not impair the hemopoietic support capacity of the feeder layers.

TABLE 8

Sensitivity of Parent and Drug-Resistant Cell Lines to Acetaldoifosphamide

| Cell line | $IC_{50}$ (uM)* | Resistance Index** |
|---|---|---|
| KBM-3 | 0.20 | — |
| KBM-3/DOX | 0.16 | 0.8 |
| KBM-3/AMSA | 0.68 | 3.4 |
| HL-60 | 0.30 | — |
| HL-60/AMSA | 0.56 | 1.9 |

*Drug added to the agar plates to allow for prolonged exposure
**Defined as: $IC_{50}$ resistant cells/$IC_{50}$ sensitive cells

TABLE 9

Regrowth of GM-CFC from Bone Marrow exposed to Acetaldoifosphamide, Then Seeded in Suspension Cultures on Autologous Irradiated Adherent Cell Layers.

| Drug Conc. uM | GM-CFC × 10⁻³ per culture at weekly intervals[s] Week | | | | | | GM-CFC × 10⁻³ per adherent cell layer[b] |
|---|---|---|---|---|---|---|---|
| | 0 | 1 | 2 | 3 | 4 | 5 | |
| 0[c] | 43.2 ± 13.4 | 22.7 ± 6.4 | 20.9 ± 9.0 | 5.9 ± 3.2 | 1.2 ± 0.8 | 0.08 ± 0.05 | 0.06 ± 0.03 |
| 0[d] | 8.7 ± 0.3 | 4.8 ± 0.3 | 4.0 ± 0.4 | 0.8 ± 0.4 | 0.1 ± 0.05 | 0.02 ± 0.008 | 0.006 ± 0.002 |
| 26.4 | 2.8 ± 1.5 | 15.0 ± 1.8 | 18.2 ± 4.6 | 2.9 ± 1.1 | 0.8 ± 0.4 | 0.09 ± 0.03 | 0.22 ± 0.09 |
| 33.0 | 0.1 ± 0.04 | 7.7 ± 1.3 | 18.6 ± 2.5 | 2.6 ± 0.3 | 1.1 ± 0.3 | 0.13 ± 0.06 | 0.12 ± 0.04 |
| 39.6 | 0.3 ± 0.2 | 16.8 ± 7.6 | 18.5 ± 6.5 | 3.9 ± 1.3 | 0.8 ± 0.3 | 0.10 ± 0.02 | 0.06 ± 0.03 |

TABLE 9-continued

Regrowth of GM-CFC from Bone Marrow exposed to Acetaldoifosphamide, Then Seeded in Suspension Cultures on Autologous Irradiated Adherent Cell Layers.

| Drug Conc. uM | GM-CFC × $10^{-3}$ per culture at weekly intervals[a] Week | | | | | | GM-CFC × $10^{-3}$ per adherent cell layer[b] |
|---|---|---|---|---|---|---|---|
| | 0 | 1 | 2 | 3 | 4 | 5 | |
| 53.0 | 0 | 0.2 ± 0.0 | 1.2 ± 0.2 | 0.3 ± 0.1 | 0.06 ± 0.02 | 0.006 ± 0.002 | 0.03 ± 0.01 |
| 0[e] | 0 | 0.4 ± 0.02 | 0 | 0 | 0 | 0 | 0 |

[a]Average values ± S.D. for three experiments. In each experiment the cultures were conducted in duplicates.
[b]At the end of the culture period. For details see Materials and Methods.
[c]Controls: $10^7$ untreated cells in a volume of 10 ml were seeded onto autologous adherent cell layers.
[d]Controls: 8 × $10^6$ XRT-treated cells (10.0 Gy) to a final volume of 10 ml seeded onto adherent cell layers.
[e]Adherent cell layers only, treated with XRT (3.0 Gy); control for GM-CFC production from the feeder layer.

Evaluation of the adherent cell layers for the presence of GM-CFC at the end of five weeks indicated that approximately half of the GM-CFC in all cultures was located within the stromal layer. The adherent cell layer from marrow cultures treated with acetaldoifosphamide concentrations at 33 uM ($IC_{99}$) contained more GM-CFC than the controls (Table 9) whereas cultures treated with acetaldoifosphamide at 39.6 uM had the same GM-CFC content as the controls. Only the marrow cultures treated at the $IC_{100}$-drug concentration (53 uM) showed a subnormal number of GM-CFC in the non-adherent as well as the adherent cell population. GM-CFC could not be recovered from flasks containing only irradiated stromal cell layers.

Figure 15:
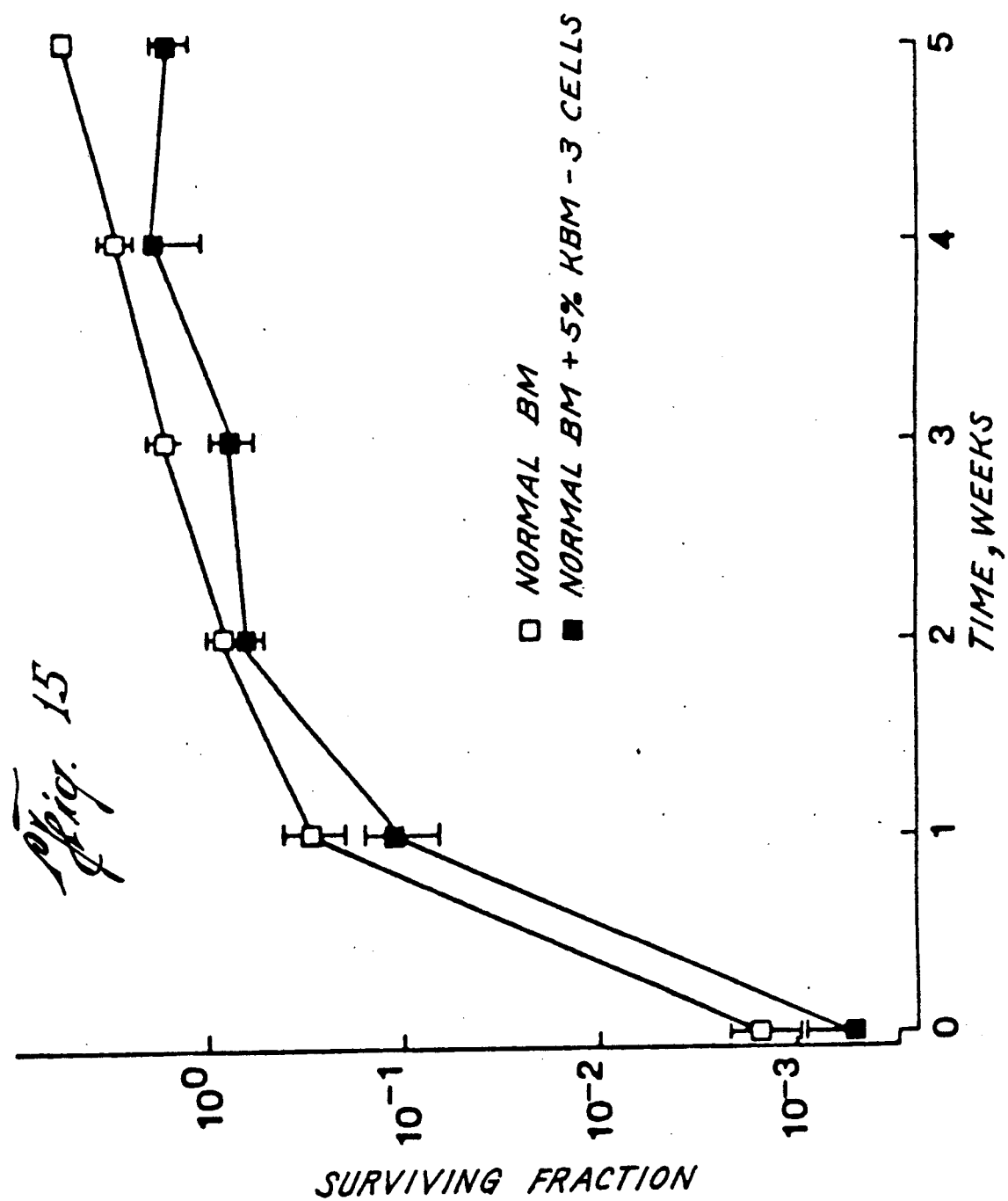
FIG. 15 shows GM-CFC production in human bone marrow in long-term suspension cultures after treatment with acetaldoifosphamide at 39.6 uM for 60 min at 37° C. Bone marrow alone, (open squares); bone marrow admixed with 5% KBM-3 cells (solid squares)-total $5 \times 10^5$ cells per culture. The drug exposure was at a concentration of $5 \times 10^6$ cells per ml in a volume of 2 ml.

The rate of GM-CFC production in marrow cultures contaminated with 5% leukemic cells (KBM-3) prior to treatment with 39.6 uM acetaldoifosphamide was the same as that of marrow alone. Significantly, no regrowth of leukemic CFC was observed during the entire 5-week observation period (See FIG. 15).

The present results indicate that the new acetal analogue of aldoifosphamide has a potential application in purging occult leukemic cells from bone marrow prior to autologous transplantation. After short-term exposure to acetaldoifosphamide or 4-HC in vitro, committed myeloid progenitors showed exponential, concentration-dependent proliferation consistent with the presumed alkylating, cell-cycle independent, mechanism of drug action. However, an eight to ten-fold difference in potency against leukemic CFC was observed between acetaldoifosphamide and 4-HC. This might be due, in part, to the different nature of the active metabolites; acetaldoifosphamide gives rise to ifosphoramide mustard while 4-HC affords phosphorodiamidic mustard. The rates of the formation of the alkylating matabolites might also differ. Thus, 4-HC generates aldoifosphamide through spontaneous chemical degradation while acetaldoifosphamide requires primary activation by carboxylate esterases (Wang et al., 1987)., Dissimilarities in the intracellular transport of the parent drugs and/or their metabolites might also account for the observed differences in potency.

In common with 4-HC, the in vitro activity of acetaldoifosphamide is dependent on the nucleated cell concentration. However, a 20-fold increase in cell concentration results in only a two-fold decrease in cytotoxicity. The presence of erythrocytes also decreases the activity of acetaldoifosphamide, a property shared with mafosfamide and 4-HC. Since all three agents undergo the same enzyme-mediated detoxification pathway this is most likely due to biotransformation by erythrocyte aldehyde dehydrogenase (Jones et al., 1987). This property mandates stringent control of experimental conditions during bone marrow purging.

Occult leukemic cells harbored in remission marrow are probably resistant to intercalating drugs, such as m-AMSA and doxorubicin, that have been used for remission induction. The sensitivity of intercalator-resistant leukemic cells to acetaldoifosphamide is a further strong indication for the use of this agent for in vitro purging.

The regrowth kinetics of GM-CFC in suspension cultures after short-term exposure of bone marrow to acetaldoifosphamide is analogous to that seen after 4-HC treatment. This kinetic pattern is distinctly different from that observed after dilution of the GM-CFC to low density, which excludes a non-specific "crowding" of the control cultures as the reason for the marked difference in proliferation. The kinetics are also markedly different from that seen after exposure of bone marrow to ionizing radiation or to an intercalating drug. It appears that acetaldoifosphamide, like 4-HC, has a sparing effect on very immature hemopoietic stem cells that cannot be directly assayed in vitro with available tissue culture techniques. In suspension cultures, however, such immature (multipotent?) stem cells would, upon recovery from sublethal damage, give rise to more differentiated progeny that seed into the GM-CFC pool during the first several days after drug exposure This might explain the early and very rapid recovery of GM-CFC. The high concentration of GM-CFC in the adherent cell layer indicates the preservation of a normal interaction between the hemopoietic progenitor cells and an intact stromal cell layer.

Remission bone marrow was simulated by adding human myeloid leukemic cells to normal marrow. The actual concentration of leukemic cells present in a remission marrow in unknown, because specific leukemic cell markers have not been described (Touw, 1986). The 5% contamination used in this study is based upon the most unfavorable accepted clinical criterion for complete remission. Despite this high concentration, the leukemia was completely eliminated with full recovery of GM-CFC production, i.e., "hemopoietic reconstitution." This corresponds to more than a 5 log reduction of leukemic cells, and appears superior to data obtained in clonogenic studies or with limiting dilution assay in similar model systems with 4-HC (DeFabriitis et al, 1985), mafosfamide (Uckun et al., 1985), or VP-16 (Stiff et al., 1987).

Although acetaldoifosphamide shares some problems with 4-HC and mafosfamide (e.g., cell density and erythrocyte concentration dependence for its in vitro cytotoxicity), it is unique in its requirement for enzymatic activation. It is considerably more potent than 4-HC.

The references in the following list as well as those cited elsewhere in this application are incorporated in pertinent part herein for the reasons cited.

REFERENCES

BERAN et al. (1987). Development and characterization of a human myelogenous leukemia cell line resistant to 4'-(9-acridinylamino)-3-methanesulfon-m-amiside. *Cancer Research* 47, 1897–1904.

BURGESS et al. (1977). Stimulation by human placenta conditioned medium of hemopoietic colony formation by human marrow cells. *Blood* 49, 573–583.

CIOBANU et al. (1986). Etoposide as an in vitro purging agent for the treatment of acute leukemias and lymphomas in conjunction with autologous bone marrow transplantation. *Experimental Hematology* 14, 626–635.

COULOMBEL et al. (1983). Enzymatic treatment of long-term human marrow cultures reveals the preferential location of primitive hemopoietic progenitors in the adherent layer. *Blood* 62, 291–297.

DE FABRITIS et al. (1985). Elimination of clonogenic Burkitt's lymphoma cells from human bone marrow using 4-hydroperoxycyclophosphamide in combination with monoclonal antibodies and complement. *Blood* 65, 1064–1070.

DELFORGE et al. (1982). Comparison of the cytotoxic effect of 4-hydroperoxycyclophosphamide on the proliferation of human normal and leukemic CFU-C. *Experimental Hematology* 10 (Suppl. 11)14.

GALLAGHER et al. (1979). Characterization of the continous differentiating myeloid cell line (HL-60) from a patient with acute promyelocytic leukemia. *Blood* 54, 713–733.

GARTNER et al. (1980) Long-term culture of human bone marrow cells. *Proceedings of the National Academy of Science USA.* 77, 4756–4759.

GLASSER et al. (1983) Purging of remission marrows with alkyl-lysophospholipids. *Blood* (Suppl. 1) 62, 794.

GORIN et al. (1986). Autologous bone marrow transplantation using marrow incubated with ASTA Z 7557 in adult acute leukemia. *Blood* 67, 1367–1376.

GREENBERG et al. (1981). Human granulocytes generated in continuous bone marrow culture are physiologically normal. *Blood* 58, 724–32.

HAGENBEEK et al. (1984). Toxicity of ASTA z 7557 (INN mafosfamide) to normal and leukemic stem cells: Implications for autologous bone marrow transplantation. *Investigational New Drugs* 2, 237–243.

HERVE' et al. (1983). Autologous stem cell grafting in acute myeloid leukemia: Technical approach of marrow incubation in vitro with pharmacological agents (prerequisite for clinical applications) *British Journal of Haematology* 53, 683–85.

JONES et al. (1987). Variability in 4-Hydroperoxycyclophosphamide activity during clinical purging for autologous bone marrow transplantation. *Blood* 70, 1490–1494.

KAIZER et al. (1985). Autologous bone marrow transplantation in acute leukemia: A phase I study of in vitro treatment of marrow with 4-hydroperoxycyclophosphamide to purge tumor cells. *Blood* 65, 1504–1510.

KORBLING et al. (1982). 4-Hydroperoxycyclophosphamide: A model for eliminating residual human tumor cells and T-lymphocytes from the bone marrow graft. *British Journal of Haematology* 52, 89–96.

KORBLING et al. (1986). Autologous transplantation of mafosfamide-purged marrow: a series of 20 patients with acute leukemia. *Bone Marrow Transplantation* 1 (Suppl. 1), 272.

KLUIN-NELEMANS et al. (1984). No preferential sensitivity of clonogenic AML cells to ASTA-Z-7557. *Leukemia Research* 8, 723–728.

ODAIMI et al. (1986). Drug sensitivity and cross-resistance of the 4,-(9-acridimylamino) methane-sulfon-m-anisidide-resistant subline of HL-60 human leukemia. *Cancer Research* 46, 3330–3333.

PIKE et al. (1970). Human bone marrow colony growth in agar gel. *Journal of Cellular Physiology* 76, 77–84.

POTTER et al. (1981). Continuous long-term culture of human bone marrow. *Clinical and Laboratory Haematology* 3, 245–30.

SANTOS et al. (1987). Autologous marrow transplantation following pharmacologic marrow purging. 4th Terry Fox Cancer Symposium, Vancouver B.C., 1987.

SLADEK et al. (1985). Restoration of sensitivity to Oxazaphosphorines by inhibitors of aldehyde dehydrogenase activity in cultured oxazaphosphorine-resistant L1210 and cross-linking agent-resistant P388 cell lines. *Cancer Res.* 45, 1549–1555.

STIFF et al. (1984). In vivo and in vitro pharmacologic purification of bone marrow contaminated with tumor cells using VP 16-213 and nitrogen mustard. Minimal Residual Disease in acute Leukemia. Ed. by Lowenberg B. and Hagenbeek A. pp. 183–88 Martinus Nijhoff Publishers, Boston.

STIFF et al. (1987). In vitro chemoseparation of leukemic cells from murine bone marrow using VP 16-213: Importance of stem cell assays. *Experimental Hematology* 15, 263–68.

TOUW (1986). Detection of minimal residual leukemia: molecular genetic, cytogenetic and immunological approaches. *Leukemia Research* 10, 69–71.

UCKUN et al. (1985). Ex-vivo elimination of lymphoblastic leukemia cells from human marrow by mafosfamide. *Leukemia Research* 9, 83–95.

WANG et al. (1987). Novel anti-tumor aldophosphamide analogs. *Proceedings of the Amer. Assoc. Cancer Res.* 28, 1018.

YEAGER et al. (1986). Autologous bone marrow transplantation in patients with acute nonlymphocytic leukemia, using ex vivo marrow treatment with 4-hydroperoxycyclophosphamide. *New England Journal of Medicine* 315, 141–147.

What is claimed is:

1. A method for purging leukemic tumor cells from bone marrow of a mammalian host, the method comprising
extracting bone marrow cells from the host;
treating extracted bone marrow cells, for a period of time and with a therapeutic level sufficient to kill leukemic cells, with a compound having the structure:

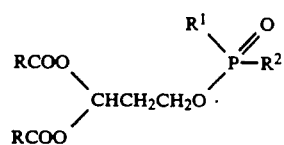

wherein:

R is —CH₃;
R¹ is —NH₂, —NHCH₃, —NHC₂H₅, —NHCH₂CH₂Cl, —N(CH₃)₂, —N(C₂H₅)₂, —OCH₃, or —OC₂H₅;
R² is —NHCH₂CH₂Cl or —N(CH₂CH₂Cl)₂; and
intravascularly infusing treated bone marrow cells into the host.

2. A method for purging leukemic tumor cells from bone marrow of a mammalian host, the method comprising:

extracting bone marrow cells from the host;

treating extracted bone marrow cells, for a period of time and with a therapeutic level sufficient to kill leukemic cells, with a compound having the structure:

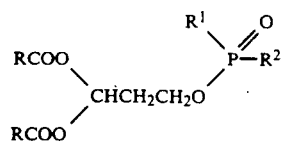

wherein:
R is —CH₃;
R¹ is —NH₂, —NHCH₃, —NHC₂H₅, —NHCH₂CH₂Cl, —N(CH₃)₂, —N(C₂H₅)₂, —OCH₃, or —OC₂H₅; and
R² is —NHCH₂CH₂Cl or —N(CH₂CH₂Cl)₂.

3. The method of claim 1 or 2 wherein the leukemic tumor cells are human leukemic cells.

4. The method of claim 1 or 2 wherein the therapeutic level is from 20 ηg/ml to 200 ηg/ml.

5. The method of claim 1 or 2 wherein the therapeutic level is about 39.6 μm.

6. The method of claim 1 or 2 wherein the leukemic tumor cells are myelogenous leukemia cells.

7. The method of claim 1 or 2 wherein the tumor cells are human myelogenous leukemia cells.

8. The method of claim 1 or 2 wherein R¹ is —NH₂ and R² is —N(CH₂CH₂Cl)₂.

9. The method of claim 1 or 2 wherein R¹ is —NHCH₂CH₂Cl, and R² is —NHCH₂CH₂Cl.

10. The method of claim 1 or 2 wherein R¹ is —OCH₃ or —OC₂H₅ and R² is —N(CH₂CH₂Cl)₂.

11. The method of claim 1 or 2 wherein R¹ is —NHCH₃, —NHC₂H₅, —N(CH₃)₂ or —N(C₂H₅)₂ and R² is —N(CH₂CH₂Cl)₂.

12. The method of claim 1 or 2 wherein the treating step involves an incubation at about 37° C. for a period of 1 to 72 hours.

* * * * *

UNITED STATES PATENT AND TRADEMARK OFFICE
CERTIFICATE OF CORRECTION

PATENT NO. : 5,055,459

DATED : October 3, 1991

INVENTOR(S) : Borje S. Andersson, David Farquhar

It is certified that error appears in the above-identified patent and that said Letters Patent is hereby corrected as shown below:

In claim 1, column 33, line 2 delete the term "-Ch$_3$" and substitute the term ---CH$_3$-- therefor.

In claim 2, column 33, line 27 delete the term "-Ch$_3$" and substitute the term ---CH$_3$-- therefor.

Signed and Sealed this

Ninth Day of February, 1993

Attest:

STEPHEN G. KUNIN

Attesting Officer

Acting Commissioner of Patents and Trademarks